(12) United States Patent
Revishvili et al.

(10) Patent No.: US 8,529,461 B2
(45) Date of Patent: Sep. 10, 2013

(54) METHOD OF NONINVASIVE ELECTROPHYSIOLOGICAL STUDY OF THE HEART

(75) Inventors: Amiran Shotaevich Revishvili, Moscow (RU); Vitaliy Viktorovich Kalinin, Voronezh (RU); Alexander Viktorovich Kalinin, Voronezh (RU)

(73) Assignee: "Amycard" LLC, Moscow (RU)

( * ) Notice: Subject to any disclaimer, the term of this patent is extended or adjusted under 35 U.S.C. 154(b) by 0 days.

(21) Appl. No.: 12/624,530

(22) Filed: Nov. 24, 2009

(65) Prior Publication Data

US 2012/0035459 A1    Feb. 9, 2012

(30) Foreign Application Priority Data

Nov. 27, 2008   (RU) ................................ 2008146996

(51) Int. Cl.
*A61B 5/0402*   (2006.01)
(52) U.S. Cl.
USPC .......................................................... 600/508
(58) Field of Classification Search
USPC .................................. 600/508, 509, 512, 513
See application file for complete search history.

(56) References Cited

U.S. PATENT DOCUMENTS

| | | | |
|---|---|---|---|
| 7,016,719 B2 | 3/2006 | Rudy et al. | |
| 2012/0004561 A1* | 1/2012 | John | 600/508 |

OTHER PUBLICATIONS

Sulimov, et al., "Transesophageal Cardiac Electrostimulation," Meditsina, pp. 78-79 (2001).

Revishvili, et al., "Electrophysiological Diagnostics and Interventional Treatment of Complex Cardiac Arrhythmias with Use of the System of Three-Dimensional Electro-Anatomical Mapping," pp. 32-37 (2003).
Pokushalov, et al., "Radio-Frequency Transpericardial Catheter Ablation of Ventricular Tachycardia", Vestnik arimologii, No. 44, pp. 58-62 (2006).
Titomir, et al., "Noninvasive Electrocardiotopography," pp. 97-111 (2003).
Nelson, et al., "The Theoretical Basis of Electrocardiology," Meditsina, pp. 346-350 (1979).
Shakin, "Computational Electrocardiography," Nauka, pp. 64-65 (1981).
Kalinin, "Use of ECG Recorded through a Subclavian Catheter for Differential Diagnosing Tachyarrhythmias," Proceedings of the 4$^{th}$ Session of the Moscow Society of Anesthesiologists and Resuscitators, Mar. 26, 2004.
Golnik, et al., "Construction and Application of Preprocessor for Generation, Performance Control, and Optimization of Triangulation Grids of Contact Systems," pp. 1-25 (2004).

(Continued)

*Primary Examiner* — George Evanisko
(74) *Attorney, Agent, or Firm* — Ladas & Parry LLP

(57) ABSTRACT

Reconstructing electrograms, whose experimental registration requires an invasive access, by computational way on unipolar ECGs recorded at 80 and more points of the chest surface. On the set of surface electrocardiograms for each discrete moment of the cardiocycle, values of the heart electric field potential at points of ECG-recording are determined, and a value of the electric field potential at each point of the chest surface is calculated by interpolation. Based on data of any visualization methodology, boundaries of chest and lungs surfaces and of the heart epicardial surface are determined. Further, a continuation of the electric field potential over the whole chest surface up to the heart epicardial surface with taking into account differences in electroconductivity of large anatomical structures of the chest is performed by computational way based on solution of the Cauchy problem for the Laplace equation in a piecewise-homogenous medium.

13 Claims, 25 Drawing Sheets

(56) References Cited

OTHER PUBLICATIONS

Denisov, "Introduction to Theory of Inverse Problems," Moscow University Publishing House, pp. 22-43 (1994).

Tikhonov, et al., "Methods of Solution of Incorrect Problems," Nauka, pp. 53-127 (1979).

Titomir, et al., "Mathematical Modeling of the Cardiac Bioelectric Generator," Nauka, pp. 329-331 (1999).

Lacroute, "Fast Volume Rendering Using a Shear-Warp Factorization of the Viewing Transformation," Computer Systems Laboratory, Depts. of Electrical Engineering and Computer Science, Stanford University, pp. 29-43 (1995).

Lorensen, et al., "Marching Cubes: A High Resolution 3D Surface Construction Algorithm," Computer Graphics, vol. 21, No. 4, pp. 163-169 (1987).

Saad, "Iterative Methods for Sparse Linear Systems," Second Edition with Corrections, pp. 2-21, 157-172 (Jul. 2000).

Rudy, et al., "The Inverse Problem in Electrocardiography: Solutions in Terms of Epicardial Potentials," Crit Rev Biomed Eng., pp. 215-268 (1988); Abstract.

Berger, et al., "Single-Beat Noninvasive Imaging of Cardiac Electrophysiology of Ventricular Pre-Excitation," Journal of the American College of Cardiology, pp. 2045-2052 (2006).

Lo, "Volume Discretization into Tetrahedra-II. 3D Triangulation by Advancing Front Approach," Computers & Structures, vol. 39, Issue 5, pp. 501-511(1991); Abstract.

Rassineux, "3D Mesh Adaption. Optimization of Tetrahedral Meshes by Advancing Front Technique," Computer Methods in Applied Mechanics and Engineering 141, pp. 335-354 (1997).

Yoshida, "Applications of Fast Multipole Method to Boundary Integral Equation Method," Dept. of Global Environment Eng., Kyoto Univ., Japan, pp. 84-86 (Mar. 2001).

Kazhdan, et al., "Poisson Surface Reconstruction," Eurographics Symposium on Geometry Processing (2006).

Schilling, et al., "Endocardial Mapping of Atrial Fibrillation in the Human Right Atrium Using a Non-contact Catheter," European Heart Journal, pp. 550-564 (2000).

Ramanathan, et al., "Noninvasive Electrocardiographic Imaging for Cardiac Electrophysiology and Arrhythmia," Nature Medicine, pp. 1-7 (2004).

Brebbia, et al., "Boundary Element Techniques: Theory and Applications in Engineering," Springer-Verlag, Chapter 2, pp. 54-122 (1984), with English translation.

MacLeod, et al., "Recent Progress in Inverse Problems in Electrocardiology," Nora Eccles Harrison Cardiovascular Research and Training Institute, University of Utah, pp. 1-20, 1998.

* cited by examiner

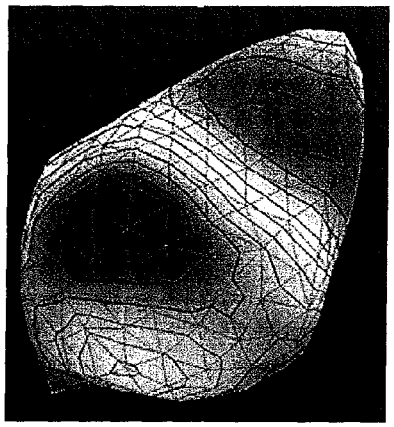

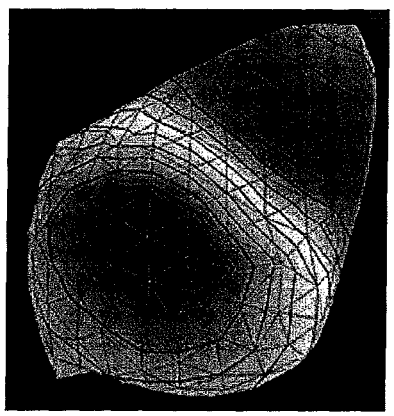

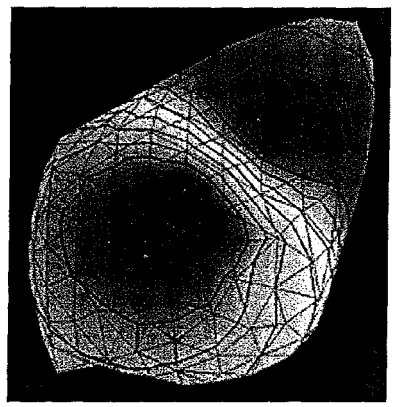

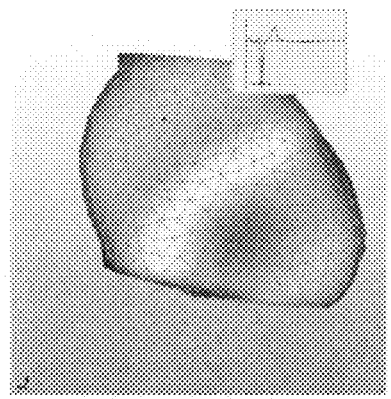 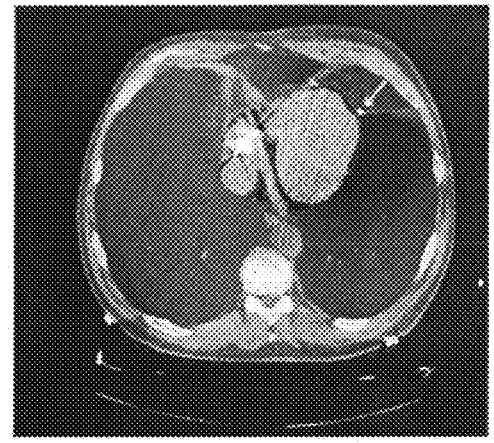
Fig. 18A　　　　　Fig. 18B
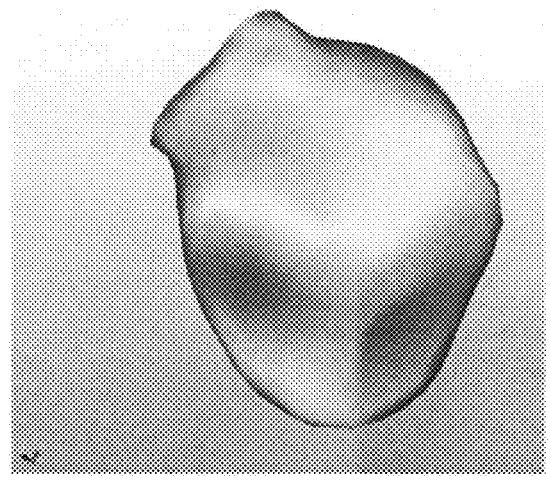
Fig. 18C

METHOD OF NONINVASIVE ELECTROPHYSIOLOGICAL STUDY OF THE HEART

FIELD OF THE INVENTION

The invention relates to medicine, namely to cardiology, cardiovascular surgery and functional diagnosis (clinical physiology), and is intended for performing a diagnosis procedure such as noninvasive electrophysiological study of the heart. More specifically, the invention is intended for reconstructing the dynamics of the heart electric field at internal points of the chest and, in particular, for obtaining intraesophageal and epicardial electrograms, as well as for performing an activation epicardial mapping, namely for obtaining epicardial isopotential and isochronous maps (myocardium activation patterns) by a noninvasive way, i.e., without inserting registration devices into heart chambers, pericardial cavity, esophageal cavity, etc.

BACKGROUND OF THE INVENTION

The most common method for diagnosis of cardiac electrophysiological processes routinely used in clinical practice is electrocardiography (ECG) in 12 standard leads. Simplicity and low cost of a standard electrocardiographical study together with its relatively high informativity have lead to its extremely widespread use in the daily practice.

However, electrocardiographical method has principled limitations. Activity of certain myocardium compartments is inadequately reflected in electrocardiographical signals registered in standard leads. As an example, one may name difficulties in ECG-diagnosis of myocardial infarction of back-basal compartments of the left ventricle. Furthermore, according to the superposition principle in electrodynamics, any electrocardiogram is the sum of electric potentials coming from sources in a great number of myocardium points. Since electrophysiological processes in different areas of the cardiac muscle proceed simultaneously, it is rather difficult to determine a local electric activity of the myocardium on standard ECG-leads. For example, an atrial re-polarization wave in humans in conditions of a normal cardiac rhythm is not revealed in ECG, as it is "hidden" by a high-amplitude QRS-complex reflecting a ventricular depolarization. A vector-electrocardiography method is characterized by the same limitations.

Greater possibilities are provided by a method for surface electrocardiographical mapping of the chest. The method consists in a synchronic registration of multiple (from 40 to 250 and more) unipolar ECG-leads from the chest surface and in constructing maps of distribution of an electric potential over the chest surface by interpolation for each discrete moment of the cardiocycle.

However, this method does not allow one to determine more precisely a local electric activity of the myocardium. If an electrode is located on the chest surface, contributions to ECG-signal from the nearest and most remote, regarding a registration electrode, segments of the myocardium differ from each other by approximately one order. For an electrode located on the heart surface, this difference is three orders. In this connection, for revealing a local electric activity of the heart, methods of invasive ECG registration are used with an attempt to bring electrodes closely to the heart surface as much as possible.

Transesophageal electrophysiological study of the heart is based on inserting a probe with registration electrodes into the esophagus cavity. The esophagus at its certain part adjoins close enough to posterior wall of the left atrium and to posterior wall of the left ventricle; therefore, intraesophageal ECG-signals selectively register the activity of these heart compartments. Intraesophageal electrocardiography is applied, in particular, for differential diagnosis of supraventricular and ventricular arrhythmias (Transesophageal electrostimulation of the heart (under edit. Sulimov V. A., Makolkin V. I.). Moscow: Meditsina, 2001.—208 pp. [in Russian]).

However, the above-mentioned method permits one to reveal a local electric activity only of individual structures of the heart.

For a complex evaluation of cardiac electrophysiological processes and topical diagnosis of cardiac rhythm disturbances, an invasive electrophysiological study of the heart based on the direct registration of a set of electrograms from epicardial or endocardial surface of the heart is carried out. Methods indicated may be applied on "open-heart" in conditions of thoracotomy, as well as on the basis of intervention technologies of inserting registration devices (catheters) into cardiac cavities by transvascular access or into pericardial cavity by its fluoroscopically-guided transskin puncture.

Up-to-date realizations of methods afore-said are directed to a precise determination of three-dimensional (3-D) coordinates of registration electrodes by non-fluoroscopic techniques and to a visualization of results in the form of isopotential and isochronous maps on heart compartment models with means of computer graphics. Computer models of heart compartments are constructed by a great number of electrogram-registration points with known coordinates, as well as on the basis of computer (CT) or magneto-resonance (MRT) tomography data of the heart (Revishvili A. Sh., Rzaev F. G., Djetybaeva S. K. Electrophysiological diagnosis and intervention treatment of complicated forms of heart rhythm disturbances with using a system of three-dimensional electroanatomical mapping.—Vestn. Aritmol. 2004, 34: 32-37 [in Russian]; Pokushalov E. A., Turov Shugaev P. L., Artemenko S. L. Radiofrequency ablation of ventricular tachycardia by transpericardial access.—Vestn. Aritmol. 2006, 44: 58-62 [in Russian]).

To this group of methods, one may refer methods for non-contact endocardial mapping based on inserting a "swimming" balloon catheter into cardiac cavities, registering a set of electrograms on the heart surface and reconstructing endocardial electrograms by computational way on data obtained (Schilling R. J., Kadish A. H., Peters N. S. et al. Endocardial mapping of atrial fibrillation in the human right atrium using a non-contact catheter.—European Heart Journal. 2000, 21: 550-564).

A disadvantage of above-disclosed methods that is eliminated by the present invention consists in their invasive character.

Analogues of the present invention are methods for reconstructing electrograms at internal points of the chest by computational way on data of synchronic registering a set of ECGs on the chest surface.

These methods are based on solution of the inverse problem of electrocardiography. Statement of the inverse problem of electrocardiography (IP ECG) is formulated in works of Barr D., Spach M Solutions of the inverse problem directly expressed in terms of potentials//Theoretical fundamentals of electrocardiology [Russian translation under edit. Nelson K. V. and Geselovitz D. V.]—Moscow: Meditsina 1979, pp. 341-352; MacLeod R. S., Brooks D. H. Recent progress in the inverse problem in electrocardiology//IEEE Eng. in Med. Bio. Mag. 17:1, pp. 78-83, January 1998; Rudy Y., Messinger-Rapport B. J. The inverse problem in electrocardiography: Solutions in terms of epicardial potentials. CRC Crit. Rev. Biomed. Eng. 1988, 16: 216-268.

From the mathematical standpoint, IP ECG is a problem of harmonic continuation (propagation) of the potential in the direction of sources, i.e., the Cauchy problem for the Laplace equation. Computational domain, in which the Laplace equation is given, represents a part of the chest bounded by heart's external surface, chest surface on which ECG-registration is accessible, and by imaginary cross-sections of the chest at the level of the diaphragm and clavicles.

At the part of the chest surface where ECG-registration is accessible values of the electric potential obtained as a result of ECG-mapping as well as the condition of equality-to-zero of a potential normal derivative are given. These data compose Cauchy conditions.

The Cauchy problem consists in finding the electric field potential in domain indicated and its trace on the heart surface and on cross-sections of the chest in such a way that the potential in computational domain would satisfy the Laplace equation, while on the torso surface where ECG-registration is accessible it would satisfy the Cauchy conditions.

According to Hadamard, the Cauchy problem for the Laplace equation is ill-posed, as any negligible errors in the condition may result in arbitrary large errors in the solution. When solving the Cauchy problem for the Laplace equation, it is necessary to apply special so-called regularizing algorithms (Denisov A. M. Introduction to the theory of inverse problems [in Russian].—Moscow: Moscow State University, 1994; Tikhonov A. N, Arsenin V. Ya. Methods for solution of incorrect problems [in Russian].—Moscow: Nauka, 1986, 312 pp.).

To solve the Cauchy problem for the Laplace equation in an above-disclosed statement (the inverse problem of electrocardiography) by an analytical way appears to be impossible. Therefore, the inverse problem of electrocardiography is numerically solved by means of computational mathematics with using computer techniques.

One of the ways for solving the inverse problem of electrocardiography is a method for reconstructing the electric field on "quasi-epicard", i.e., on a conditional spherical surface surrounding the heart. From the mathematical standpoint, this method is based on representation of the heart electric field potential in the form of a harmonic polynomial (sphere function), whose coefficients are found from the condition of equality (or the minimum of mean square deviation) of polynomial values and values of an ECG-signal at points of its registration with taking into account the equality-to-zero of a potential normal derivative on the chest surface. For providing the stability of solution, a polynomial of degree not higher than 4 is used. An essential disadvantage of this method is that, when the radius of sphere diminishes, i.e., as "quasi-epicard" surface approximates to a real surface of the heart, the accuracy of potential reconstructing sharply drops. When "quasi-epicard" surface approximates to the chest surface, the resolution of the method in terms of revealing a local electric activity of the myocardium decreases (Titomir L. I., Kneppo P. Mathematical modeling of heart's bioelectric generator.—Moscow: Nauka, Physmathlit, 1999.—448 pp. [in Russian]; Titomir Trunov V. G., Aidu E. A. I. Noninvasive electrocardiography.—Moscow: Nauka, 2003.—198 pp. [in Russian]).

For solving boundary problems for the Laplace equation, methods of integral equations of the potential theory, more known in English-written literature as boundary element methods, are widely used (Brebbia C., Telles J., Wrobel L. Boundary element methods [Russian translation].—Moscow, Mir, 1987). The present approach to IP ECG solution is proposed in works of Taccardi E., Plonzi R., Barr R. (Barr R., Spach M. Inverse problem solutions directly expressed in terms of a potential//Theoretical fundamentals of electrocardiography [Russian translation under edit. Nelson C. V. and Geselovitz D. V.]—Moscow: Meditsina, 1979; pp. 341-352). Above-mentioned methods suppose, in particular, the representation of the heart and torso surfaces as polygonal ones, i.e., splitting boundary surfaces into a great number of triangular elements. According to the boundary element method, IP ECG for a homogeneous model of the chest is reduced to solving a system of two Fredholm integral equations of $1^{st}$ and $2^{nd}$ kinds, which is approximately substituted by a system of matrix-vector equations:

$$A_{11}x + A_{12}y = c_1,$$

$$A_{21}x + A_{22}y = c_2 \qquad (1)$$

where $A_{i,j}$ are known matrices, $x_1$, $x_2$ are unknown vectors having a sense of sought-for values of the potential and its normal derivatives in nodes of triangulation grids approximating the heart surface and torso cross-section surfaces, $c_1$, $c_2$ are known vectors calculated on known data of the problem.

In the method for noninvasive epicardial mapping suggested by Shakin V. V. et al. the following algorithm of IP ECG solution was used.

The system of matrix-vector equations (1) by means of elementary transformations was reduced to a system of linear algebraic equations (SLAE) to be resolved in explicit form:

$$\Phi_H = Z_{HB} \cdot \Phi_B, \qquad (2)$$

where $\Phi_H$ is an unknown vector having a sense of sought-for values of the potential and its normal derivatives in nodes of triangulation grids approximating the heart surface and torso cross-section surfaces, $Z_{HB}$ is a known matrix, $\Phi_B$ is a known vector. For calculating matrix $Z_{HB}$, it is necessary to use an inversion procedure of matrices entering the system (1), one of matrices to be inversed being non-square and bad-conditioned. For implementation of this procedure, constructing a Moore-Penrose pseudo-inverse matrix on the basis of SVD-decomposition of an initial matrix and substituting small singular values by zeroes were performed.

The heart and torso surfaces were represented as simplified models in the form of cylindrical and ellipsoidal surfaces to be constructed on the basis of two-projection roentgenography of the chest. Results of mapping in the form of isopotential and isochronous maps were imposed on model scanned-schemes of heart compartments. This methodology was used for revealing a localization of additional pathways (APW) at manifested WPW syndrome and ectopic sources at ventricular extrasystole (Shakin V. V. Computational electrocardiography [in Russian].—Moscow: Nauka, 1980).

In his works, Shakin V. V. has emphasized a promising outlook of the application of computer-tomography techniques for more precise constructing the torso and heart surfaces; however, this approach could not be used because of unsatisfactory development of methods for computer tomography of the heart.

The most similar to a method claimed here (prototype) is the methodology of noninvasive electrocardio graphical imaging (ECGI).

In this methodology, a surface mapping is realized with using 224 unipolar electrodes placed in a special vest to be put on a patient for a study period. The torso and heart surfaces is determined based on computer (CT) or magneto-resonance (MRT) tomography of the chest. A reconstruction algorithm is based on solution of the inverse problem of electrocardiography by the boundary element method.

The torso and heart surfaces is approximately represented as polygonal surfaces. For solving IP ECG, the system of matrix-vector equations (1) is also used, which by elementary transformations is reduced to a system of linear algebraic equations $$Ax = c \qquad (3)$$

where x is an unknown vector having a sense of sought-for values of the potential in nodes of triangulation grids approximating the heart surface and torso cross-section surfaces, A is a known matrix, c is a known vector.

The system of linear algebraic equations (3) is bad-conditioned. For its solving the Tikhonov regularization method and the iteration regularization method on the basis of GMRes-algorithm are used. The Tikhonov method is based on solving the following system instead of the system (3)

$$(A^T \cdot A + \alpha E)x = A^T c$$

where $A^T$ is a matrix transponated in respect to matrix A, E is an unit matrix, α is a regularization parameter (a small positive real number).

The iteration regularization method is based on solution of the system (3) by a method of sequential approximations with limiting a number of iterations on the basis of GMRes-algorithm, which belongs to a group of Krylov subspace methods (Ramanathan C., Ghanem R. N., Jia P., Ryu K, Rudy Y Electrocardiographic Imaging (ECGI): A Noninvasive Imaging Modality for Cardiac Electrophysiology and Arrhythmia//Nature Medicine, 2004; 10: 422-428; Rudy Y., Ramanathan, C., R. N. Ghanem, R. N., Jia P. System and Method For Noninvasive Electrocardiographic Imaging (ECGI) Using Generalized Minimum Residual (GMRes)// U.S. Pat. No. 7,016,719 B2, 2006).

The similar technique was used in works of Berger T., Fisher G., Pfeifer B. et al. Single-Beat Noninvasive Imaging of Cardiac Electrophysiology of Ventricular Pre-Excitation// J. Am. Coll. Cardiol., 2006; 48: 2045-2052.

This technique was applied for revealing an APW-localization at manifested WPW syndrome, ectopic sources at ventricular extrasystole and tachycardia, reconstruction of an activation dynamics of the myocardium at atrium flutter.

The essential disadvantage of the method under consideration is using a model of the chest with a constant (invariable) coefficient of specific electroconductivity. Specific electroconductivity of different organs and tissues of the chest shows essential distinctions. A variable electroconductivity coefficient of biological tissues strongly enough influences on the heart electric field in the chest what is confirmed by data of experimental research (Rudy Y., Wood R., Plonsey R., Liebman J. The effect of high lung conductivity on electrographic potentials. Results from human subjects undergoing bronchopulmonary lavage//Circulation 1982, 65: 440-445). The greatest role plays the difference in electroconductivity between lungs and surrounding them soft tissues (at 4-5 times). Potentials of the heart electric field of model sources calculated for homogeneous and inhomogeneous models of the chest differ from each other by 15%-20% (Titomir L. I., Kneppo P. Mathematical modeling of heart's bioelectric generator.—Moscow: Nauka, Physmathlit, 1999.—448 pp. [in Russian]. Thus, neglect of an electrical inhomogeneity of chest tissues may lead to greater errors of reconstructing the heart electric field.

The present invention is aimed at improving the accuracy of noninvasive electrophysiological study of the heart at the expense of taking into account a different electroconductivity coefficient of chest tissues.

SUMMARY OF THE INVENTION

For carrying out an electrophysiological study of the heart, a registration of a set of electrograms from the heart surface is necessary based on which isopotential, isochronous maps are constructed and electrophysiological processes in the cardiac muscle are diagnosed. In order to obtain these electrograms an invasive way, i.e., inserting special registration devices into heart chambers or pericardial cavity, is used.

The present invention consists in reconstructing electrograms, whose experimental registration requires an invasive access, by computational way on unipolar ECGs recorded at 80 and more points of the chest surface. Based on a set of surface electrograms for each discrete moment of the cardiocycle, values of the heart electric field potential at points of ECG-recording are determined, and a value of the electric field potential at each point of the chest surface is calculated by interpolation. On data of any visualization methodology (computer tomography (CT), magneto-resonance tomography (MRT)) boundaries of the chest surface, epicardial surface of the heart and large anatomical structures of the chest, as well as average values of specific electroconductivity of tissues of chest organs are determined.

Further, a continuation of the electric field potential throughout the whole surface of the chest up to the heart's epicardial surface is implemented by computational way on the basis of solution of the Cauchy problem for the Laplace equation in an inhomogeneous medium. For solving the Cauchy problem for the Laplace equation a model of the chest is used with tissues that within the bounds of large anatomic structures (lungs, mediastinum, spine) have an averaged constant coefficient of electroconductivity. For all that, the heart electric field potential is a harmonic function in each of regions with a constant coefficient of electroconductivity and satisfies conjugate conditions (continuity conditions of potential and current) at the border of regions.

For solving the Cauchy problem for the Laplace equation, the boundary element method is applied; on its basis, an initial problem is reduced to a problem of solving a system of matrix-vector equations. In order to improve the accuracy of the method, an iterative algorithm of solution of a system of matrix-vector equations is used. At each step of an iteration procedure, a system of linear algebraic equations (SLAE) is solved on the basis of regularizing algorithms. For performing an operation of matrix-vector multiplication, the "fast multipole method" is applied which allows one to increase rather significantly the rate of calculations for matrices of high size.

The above-written sequence of procedures is repeated for each discrete moment of the cardiocycle. On obtained values of the potential at given internal points of the chest, required electrograms are reconstructed by interpolation. Based on reconstructed electrograms, isopotential, isochronous maps on realistic models of the heart are constructed, a dynamics of the myocardium excitation is reconstructed and diagnosis of electrophysiological processes in the cardiac muscle is performed.

BRIEF DESCRIPTION OF FIGURES

FIG. 5 (continued). In upper drawing an isoline drift is shown, in lower one—a resulting filtered signal.

FIG. 17 (continued) compares the running time for implementation of a classical algorithm BEM and of FMM BEM.

DETAILED DESCRIPTION OF PREFERRED EMBODIMENTS

To provide a comprehensive understanding of the invention, its specific illustrative embodiments are described below; however, those of ordinary skill in the art have to recognize that methods and systems may be modified within the scope of the invention as defined by the appended claims.

Methods and systems disclosed here use a device of surface ECG mapping, visualization techniques of computer (CT) or magneto-resonance (MRT) tomography, computing techniques, as well as mathematical algorithms of solution of the inverse problem of electrocardiography for non-invasive reconstructing electrograms at internal points of the chest and on the heart's epicardial surface and for constructing isopotential and isochronous epicardial maps on a realistic three-dimensional (3-D) computer model of the heart.

Figure 1:
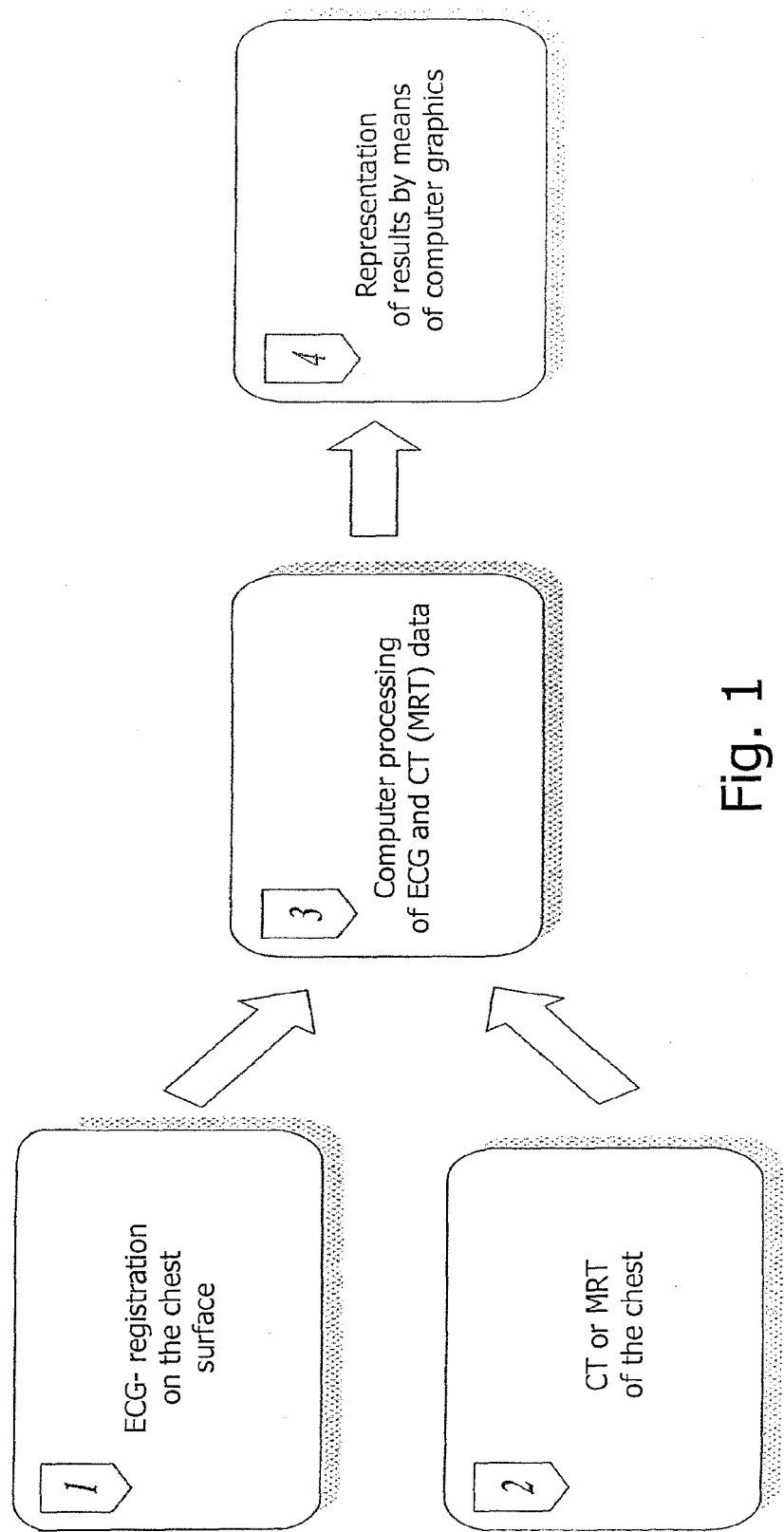
FIG. 1 illustrates a general scheme of the method.

FIG. 1 illustrates a general schematic view of the method. The method includes (1) a registration of from 80 to 240 unipolar ECG on the chest surface, (2) an implementation of CT or MRT of the chest, (3) data processing of surface ECG mapping and CT (MRT) using means of computing techniques and (4) a representation of the obtained electrophysiological information with computer graphics means.

Figure 2:
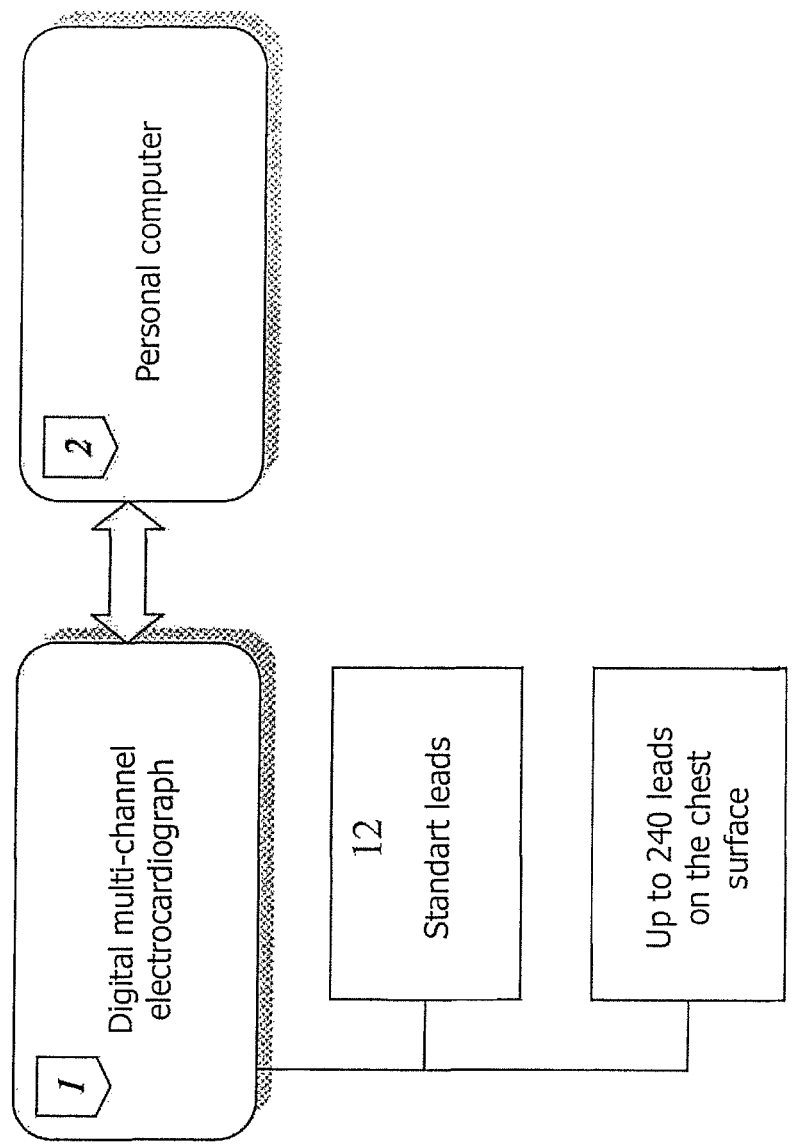
FIG. 2 shows a schematic view of the methodology of surface ECG mapping.

FIG. 2 illustrates a schematic view of the methodology of surface ECG mapping. A mapping device comprises a digital multi-channel electrocardiograph (1) connected with a personal computer (2). The digital multi-channel electrocardiograph allows one to register ECG-signals in 12 standard leads and in up to 240 unipolar leads from the chest surface.

Figure 3:
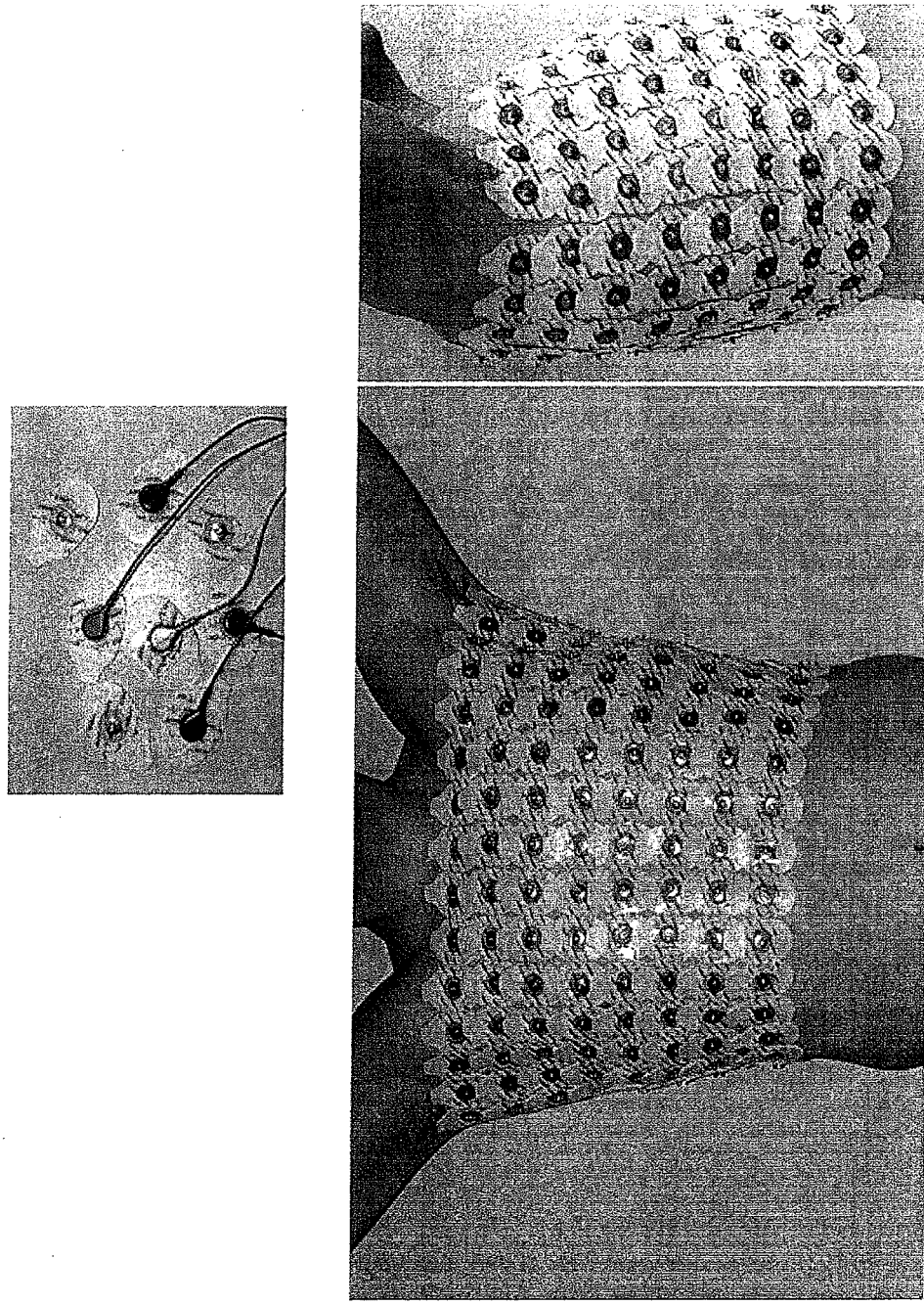
FIG. 3 illustrates a scheme of imposing electrodes on the chest surface.

FIG. 3 illustrates a scheme of superimposing electrodes. For surface ECG mapping, one-off metal chlorine-silver electrodes (at computer tomography) or one-off graphite ones (at magneto-resonance tomography) are used (1). Electrodes are imposed in the form of 5-8 horizontal belts (strips) positioned at similar distances along the vertical. The upper strip is located at the level of sterno-cleidal articulation, the lower one—at the level of lower edge of rib-arch. Each strip includes from 16 to 30 electrodes located at similar distances in circumference of the chest (2).

Figure 4:
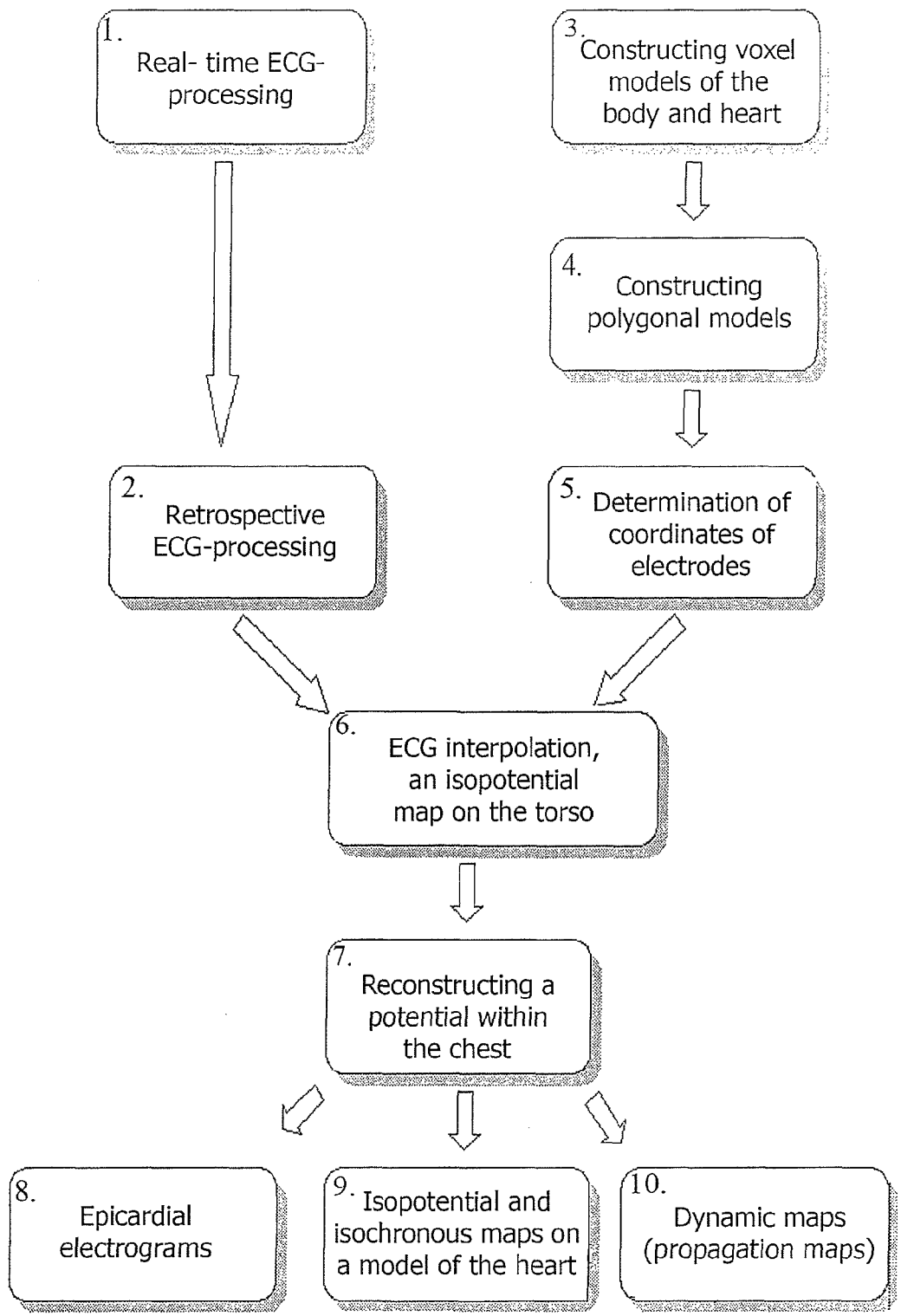
FIG. 4 presents the main stages of computer processing of the information.

FIG. 4 depicts the main stages of computer processing of the information.

The stage (1) is a real-time processing of ECG-signals in the course of multi-channel ECG registration from the chest surface. The stage (2) is a retrospective processing of ECG-signals. The stage (3) includes constructing voxel models of the chest, heart and its compartments on CT or MRT data. The stage (4) comprises constructing polygonal surfaces of the chest, heart and its compartments. The stage (5) includes an automatic determination of coordinates of registration electrodes on the chest surface according to CT or MRT data. At stage (6) a surface interpolation of values of surface mapping ECG-signals at each discrete moment and a construction of isopotential maps on the chest surface are performed. The stage (7) comprises a computational reconstruction of the heart electric field potential at internal points of the chest and on the heart's epicardial surface. At the last stage, reconstructing epicardial electrograms (8) and constructing epicardial isopotential, isochronous maps using computer graphics means (9) on a realistic computer model of the heart and visualizing the dynamics of electrophysiological processes of the myocardium in animation mode (propagation mapping) (10) are performed, respectively.

Figure 5:
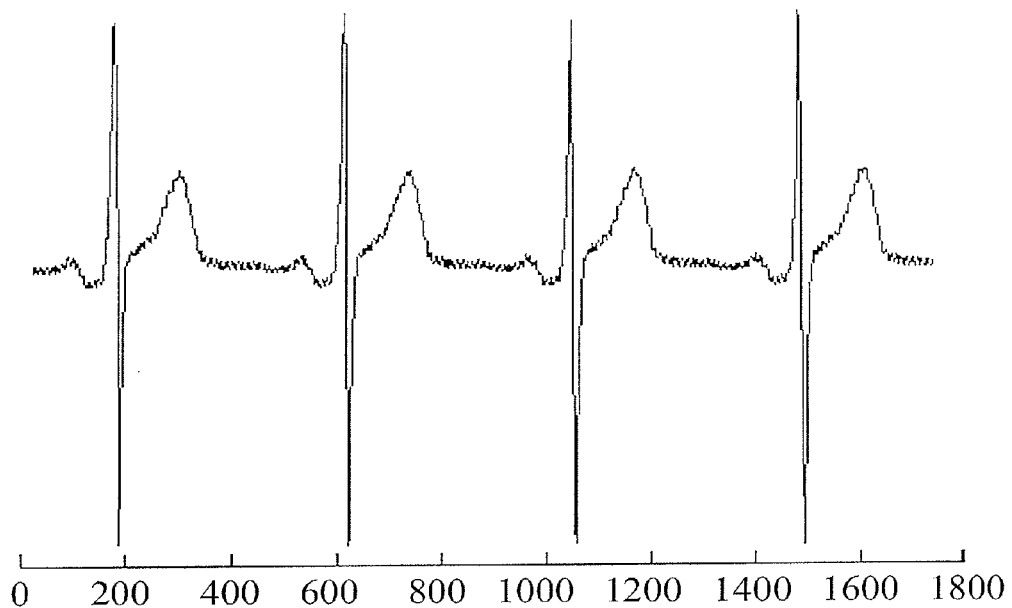
FIG. 5 illustrates processing of ECG signals in the course of ECG mapping in real-time mode. In upper drawing power-line noises are shown, in lower one—muscle noises.
Figure 5:
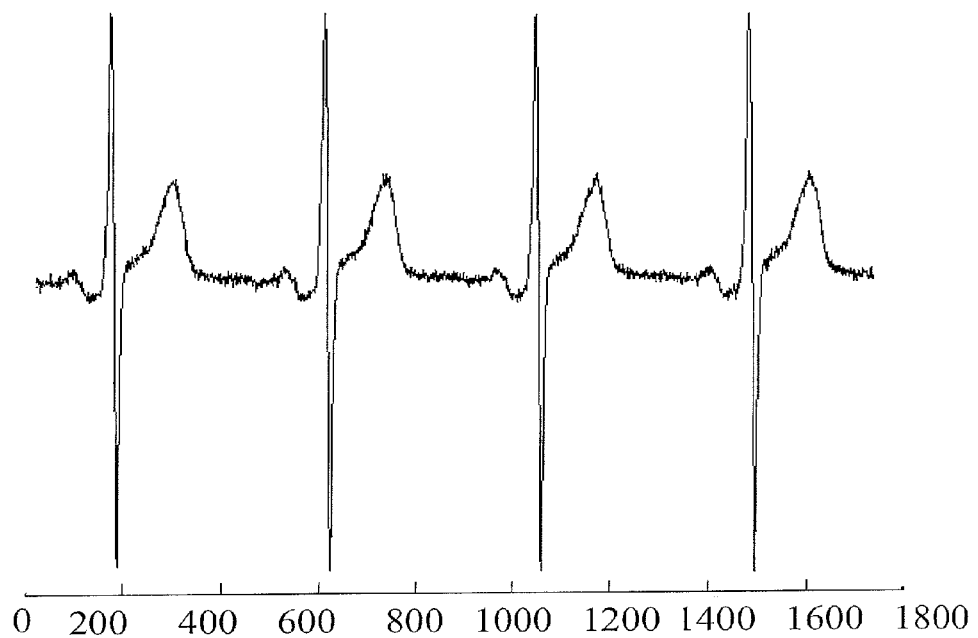
Figure 5:
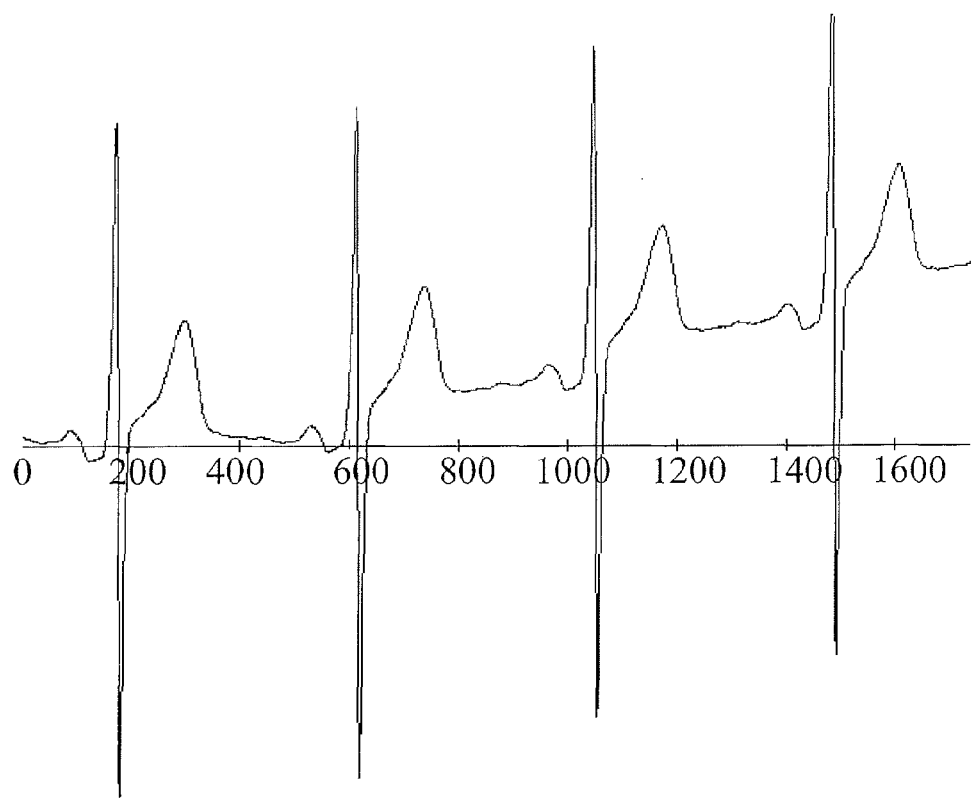
Figure 5:
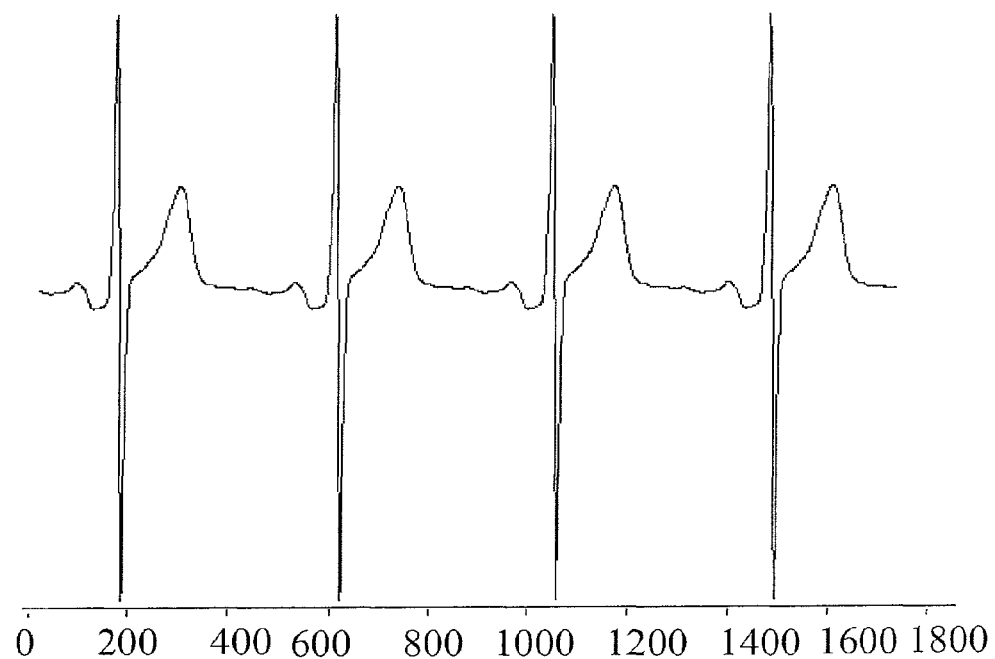

FIG. 5 illustrates processing of ECG-signals in the course of real-time ECG mapping. ECG-signals registered are reflected in a computer display. An operator controls the quality of an ECG-signal in each of the leads; if necessary, a programmed suppression of power-line (1) и muscle (2) noises and of an isoline drift (3) is applied. Automatic control of the contact of an electrode with skin and of correctness of imposing electrodes is also performed based on spectral and mutual-correlation analyses of ECG-signals. Results of the stage (1) are digitalized and filtered values of ECG-signals in 80-240 unipolar leads from the chest surface and in 12 standard leads with a duration up to 3 minutes.

Figure 6:
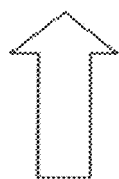
FIG. 6 illustrates a retrospective processing of ECG-signals.
Figure 6:
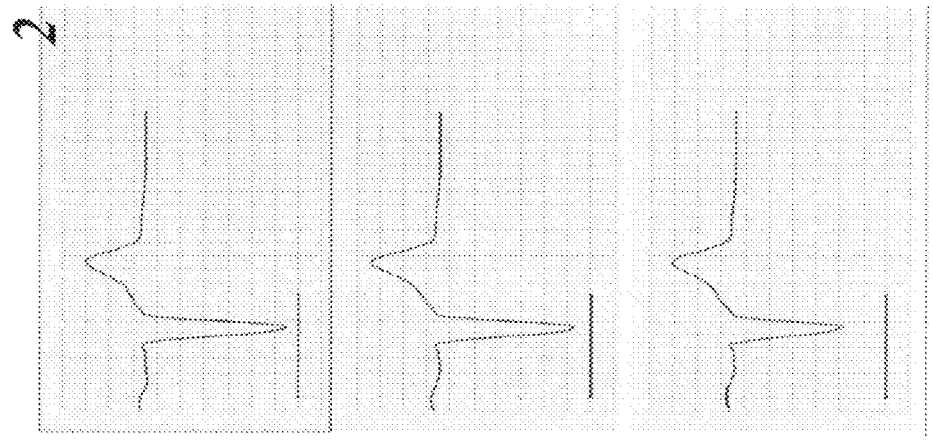
Figure 6:
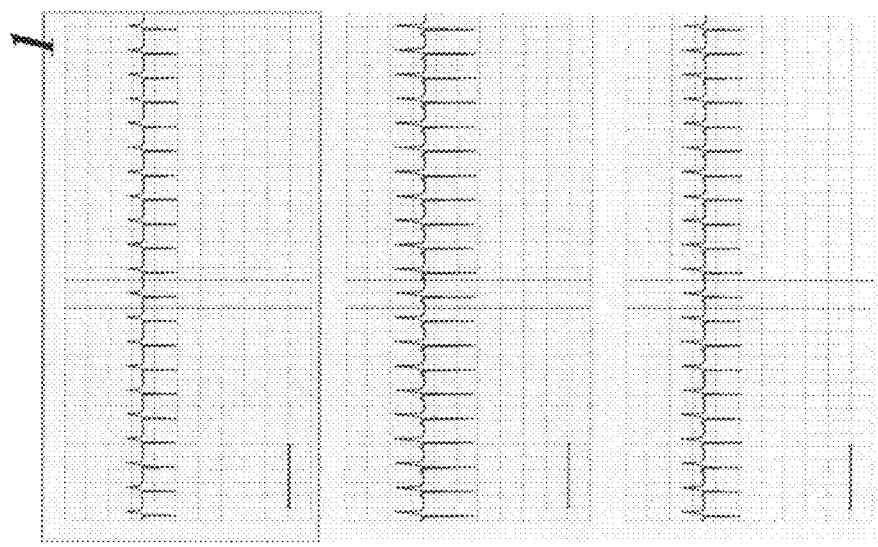
Figure 6:
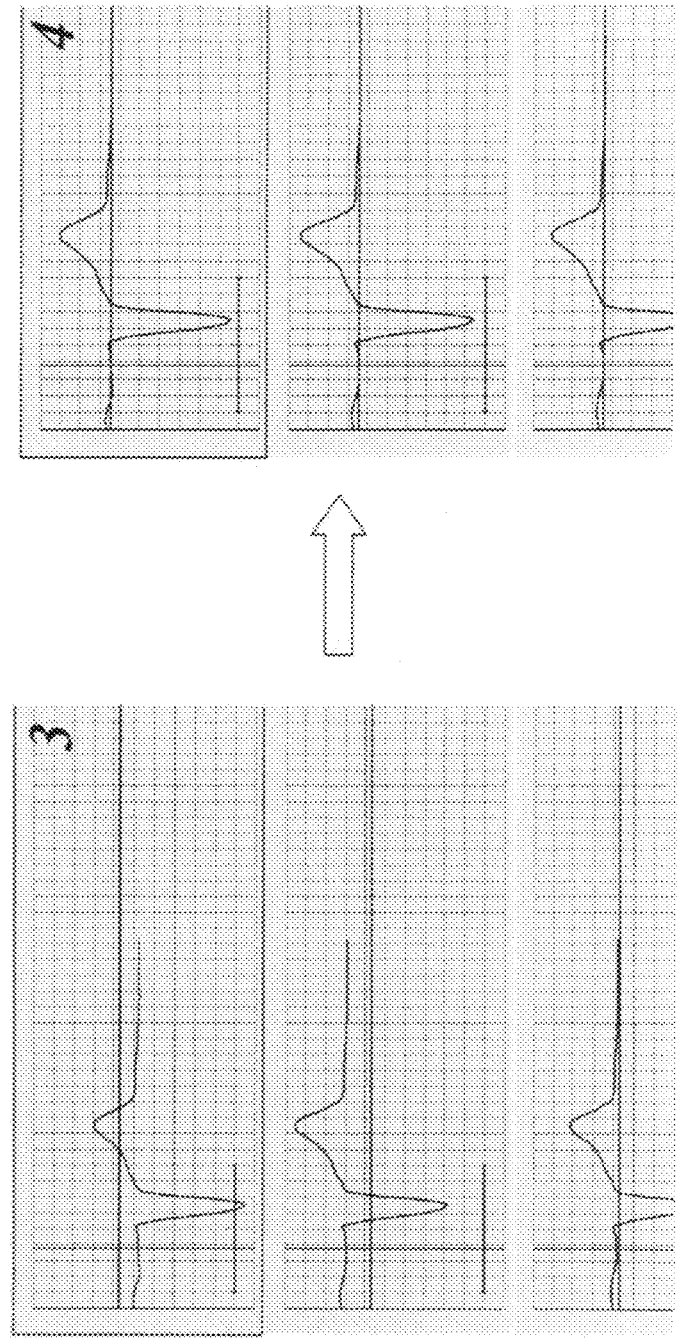

FIG. 6 depicts a retrospective processing of ECG-signals.

An operator looks through ECG-signals registered and chooses one or several cardiocycles for posterior processing (1,2). Further, a reduction of ECG to a unity isoline (3, 4) is implemented: to this end, the operator in one of ECGs chooses such a time interval τ within which an ECG-signal coincides with an isoline (as a rule, this interval belongs to the segment PQ). Correction of ECG signals is performed according to the formula:

$$U_0(t) = U(t) - u_0,$$

where $U_0(t)$ is a corrigiert ECG-signal, $U(t)$ is an initial ECG-signal, $u_0$ is an average value of an initial ECG-signal at a time interval τ.

Afterwards, the operator chooses a fragment under interest of the cardiocycle for subsequent calculations.

Figure 7:
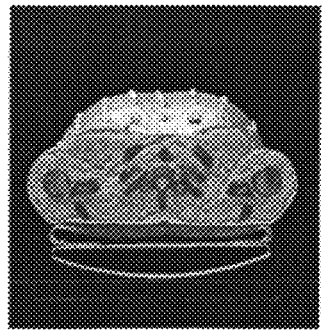
FIG. 7 shows constructing a voxel model of the torso, heart and lungs in voxel graphics editor.
Figure 7:
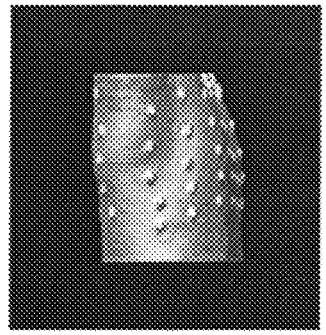
Figure 7:
Figure 7:
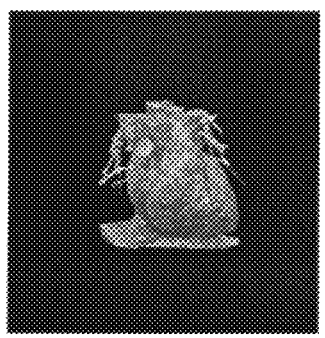
Figure 7:
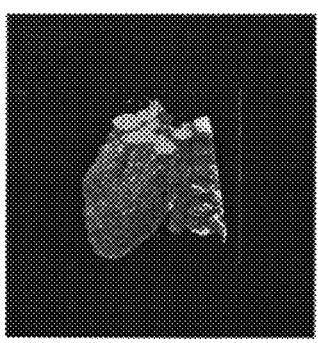
Figure 7:
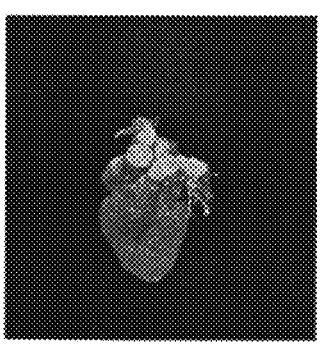
Figure 8A:
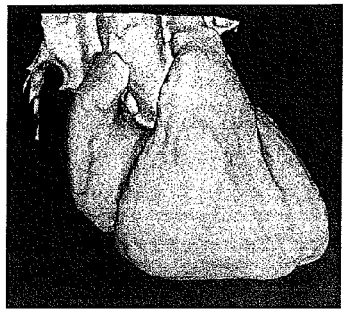
FIG. 8A: in the left column stages of constructing a polygonal grid of the heart are shown: an initial grid (350 000 elements), a reconstructed grid (20 000 elements), and a rarefied grid (3 000 elements). In the right column stages of constructing a polygonal grid of the torso are shown: an initial grid (900 000 elements), a reconstructed grid (20 000 elements), and a rarefied grid (3 000 elements).
Figure 8A:
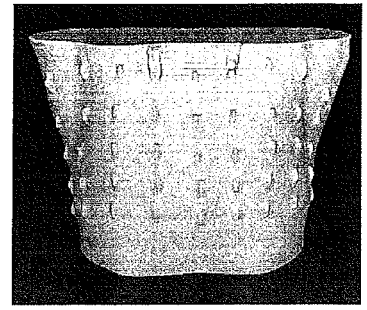
Figure 8A:
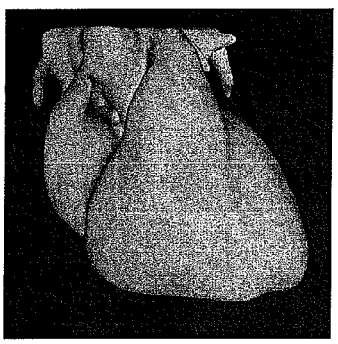
Figure 8A:
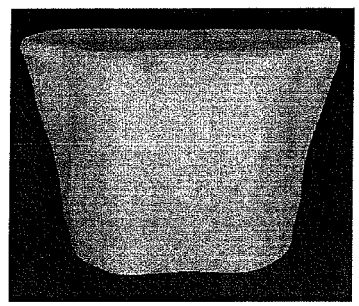
Figure 8A:
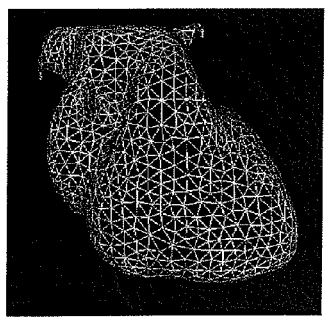
Figure 8A:
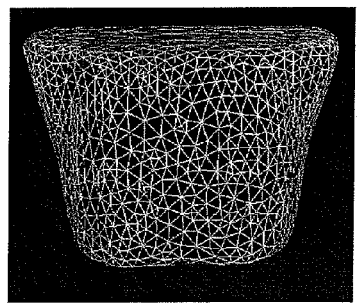
Figure 8B:
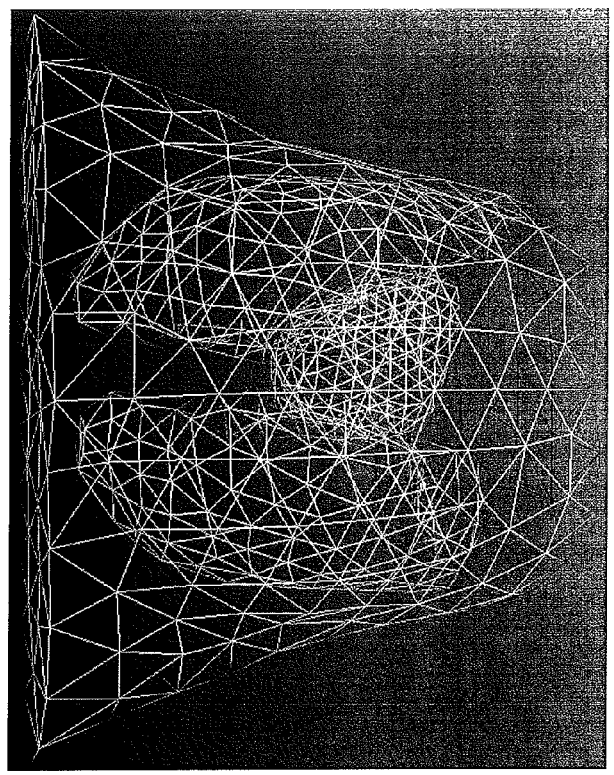
FIG. 8 illustrates constructing polygonal surfaces (triangulation grids) of the torso, heart (8A) and lungs (8B) based on voxel models.
Figure 8B:
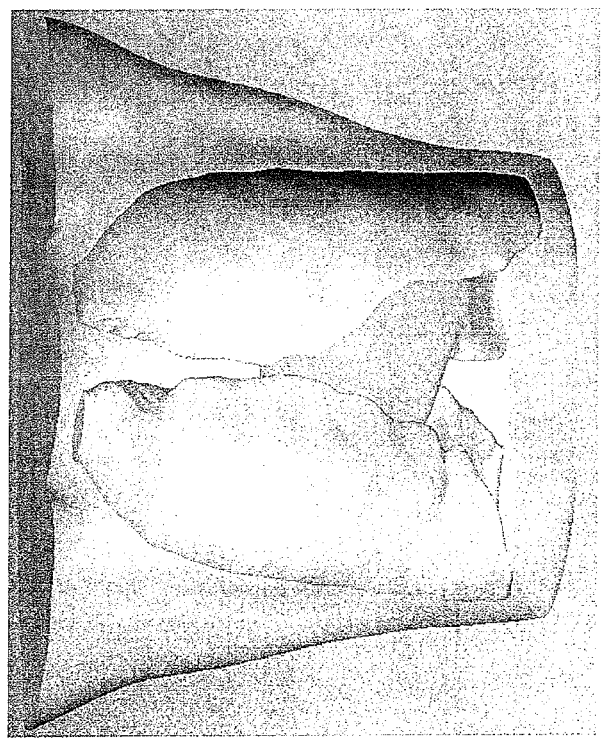
Figure 9:
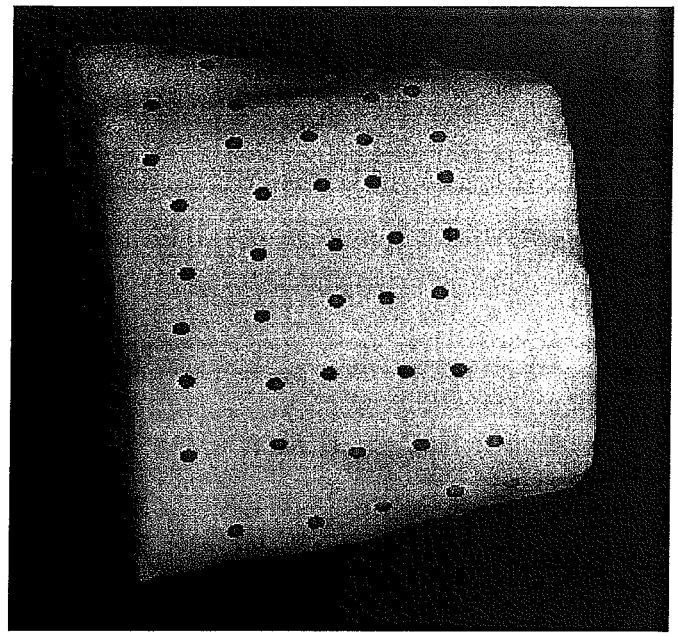
FIG. 9 shows an automatic determination of electrode coordinates on CT or MRT data of the chest.
Figure 9:
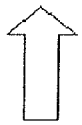
Figure 9:
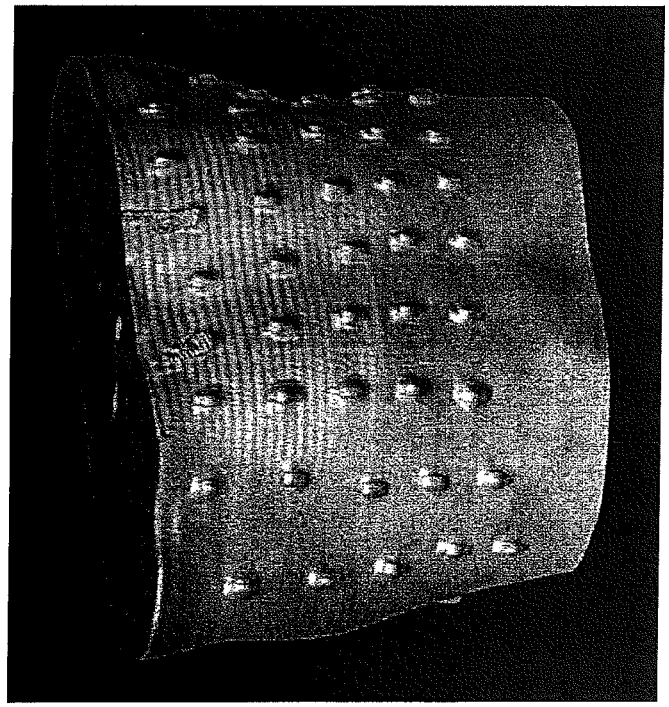

FIG. 7 illustrates constructing a voxel model of the torso and heart in voxel graphics editor.

On CT or MRT data of the chest and heart a voxel rendering of anatomical structures of the chest is realized. For this purpose a "shear-warp factorization" for the viewing transformation algorithm, which belongs to a group of scanline-order volume rendering methods, is used.

The concept of the voxel rendering method applied here consists of three main steps (Philippe Lacroute Fast Volume Rendering Using a Shear-Warp Factorization of the Viewing Transformation.—Ph.D. dissertation, Technical Report CSL-TR-95-678, Stanford University, 1995).

At first step, volume data are transformed by a shear matrix in the corresponding object space, each parallel slice of volume data after transformation passing through a special filter for diminishing distortions.

At second step, an intermediate 2D image within the same shear space is formed from a combined set of filtered and sheared slices by their direct-order superposition.

At third step, the intermediate 2D image obtained is transferred in a normal image space with using a shear matrix and, further, it again passes through a filter for formation of a final image.

An operator using instruments of voxel edition makes ready a voxel model of the torso, heart and one of its structures.

FIG. 8 illustrates constructing polygonal surfaces (triangulation grids) of the torso, heart and lungs based on voxel models.

On the basis of obtained voxel models, polygonal surfaces consisting of united planar triangles are automatically constructed. Initial data represent a three-dimensional scalar field of densities in a voxel representation, i.e., a three-dimensional right-angled grid, in nodes of which values of conditional densities of chest tissues are given. Constructing triangulation grids of the torso and organs of the chest represents a construction of polygonal surfaces that by the nearest way repeat surfaces of afore-said structures given by the definite level of a density.

A procedure of constructing polygonal surfaces comprises the following stages:
  filtrating initial voxel models for diminishing a casual noise level;
  constructing a triangular surface on the basis of a <<marching cubes>> and of <<exhaustion method>> algorithm, more known in English-written literature as an <<advancing front>> algorithm (1);
  smoothing the grid, i.e., constructing a polygonal surface similar to initial one but differing from it by lower values of angles between normal vectors of adjacent triangles (2);
  rarefying and quality-improving a grid, i.e., constructing a polygonal surface with a lower number of more large triangles that, in their turn, are the most similar to equilateral ones (3).

<<Marching cubes>> algorithm allows one to construct a polygonal representation of isosurfaces given by a three-dimensional scalar field of densities (W. Lorensen, H. Cline Marching Cubes: A High Resolution 3D Surface Construction Algorithm Computer Graphics, 21 (4): 163-169, July 1987).

The space is examined by displacing a construction cube. At each step, density values are determined in vertices of this cube. When a density value in one of vertices of a cube edge is lower and in another one is higher than an isolevel, it is concluded that a surface intersects this edge. After comparing values of densities for all vertices of a construction cube, it is determined what edges are intersected by an isosurface. Every variant of intersecting a construction cube by an isosurface defines a known set of triangles, which are added into a resultant grid.

For improving the quality of a triangulation grid, an <<advancing front>> algorithm is used, with the help of which constructing a new grid with monitored parameters is implemented on the basis of the grid obtained by the <<marching cubes>> method. The <<advancing front>> algorithm is described in more detail in Lo S. H. Volume Discretization into Tetrahedra—II. 3D Triangulation by Advancing Front Approach//Computers and Structures, Pergamon, Vol. 39, No. 5, p.p. 501-511, 1991; Rassineux A. Generation and Optimization of Tetrahedral Meshes by Advancing Front Technique//International Journal for Numerical Methods in Engineering, Wiley, Vol. 41, p.p. 651-674, 1998; Gol'nik E. R., Vdovichenko A. A., Uspekhov A. A. Construction and Application of a Preprocessor of Generation, Quality Control, and Optimization of Triangulation Grids of Contact Systems//Information Technologies, 2004, No. 4, p. 2-10 [in Russian].

Algorithm of smoothing a triangulation grid consists in the following. For each node of a grid with coordinates $P_0 = (x_0, y_0, z_0)$, N of the nearest nodes $P_j = (x_j, y_j, z_j)$, j=1, 2, ..., N are determined. The point Q=(x, y, z), which is an averaged position of this node $P_0$ and its neighbors, is computed:

$$Q = \frac{\sum_{j=0}^{N} P_j}{N+1}.$$

Further, for the node $P_0$ a vector r directed from this node to the point Q is computed. At each i-th step of an iterative process $P_0$ displaces to the direction of the vector r:

$$P_0^{(i+1)} = P_0^{(i)} + \tau^{(i)} \cdot r^{(i)}.$$

The choice of a parameter τ is implemented so that a new node $P_0^{(i+1)}$ would be maximally close to the point $Q^{(i)}$ with consideration of the following limitation: displacement vector $\tau^{(i)} \cdot r^{(i)}$ has not to overstep the boundaries of a construction cube used in the marching cubes algorithm: $\|\tau^{(i)} \cdot r^{(i)}\| < \lambda$ where $\| \ldots \|$ is the Euclidean norm of a vector, λ is the edge length of a construction cube.

This operation is repeated until the displacement of a node at i-th iteration gets less than a given value of stopping $\epsilon$ $$\|\tau^{(i)} \cdot r^{(i)}\| < \epsilon.$$

Algorithm of constructing a smoothed isosurface based on solution of the Poisson equation is also used. (M. Kazhdan, M. Bolitho and H Hoppe Poisson Surface Reconstruction.—Eurographics Symposium on Geometry Processing, 2006). This algorithm may be applied to both an initial voxel field and a triangulation surface of poor quality.

A hierarchical splitting of the space into cubic regions, i.e., constructing an oct-tree, is implemented so that each terminal branch of oct-tree contains nor more than N elements. A pronounced smoothing effect depends on the number N. Grid's nodes are considered as oriented points (of vector) $V_i$ equal to unit normal vectors to the surface to be approximated. In the center of each j-th cubic element so-called three-dimensional radial basis function (RBF) is defined.

As RBF, it is possible to use the Cauchy function $$f_j(x) = \frac{1}{1 + \|\bar{x}_j - x\|^2}$$

where $\bar{x}_j$ is the center of a cubic element, x is a random point of the space, $\|\ldots\|$ is the Euclidean distance between points, as well as three-dimensional RBF of other kinds based on the Gaussian curve, etc.

In a computational domain, $\Omega$, a vector field $U(x)=(U_x(x), U_y(x), U_z(x))^T$ is introduced. This vector field is represented in the form of decomposition by a system of RBF functions:

$$U_x(x)=\Sigma a_j \cdot f_j(x), U_y(x)=\Sigma b_j \cdot f_j(x), U_z(x)=\Sigma c_j \cdot f_j(x)$$

where $a_j$, $b_j$, $c_j$ are indefinite coefficients that are found from the condition for the minimum of mean-square deviation of vector-function U(x) from vectors $V_i$.

On the basis of the obtained vector-function U(x) a scalar function $\phi(x)$, which satisfies the condition: arg min$\|$grad$\phi$(x)−U(x)$\|_{L_2}$, is found. The function $\phi(x)$ is found as solutions of the Poisson equation:

$$\Delta\phi(x)=q(x)$$

in a computational domain $\Omega$ with its own boundary conditions where q(x)=divU(x).

For solving the Poisson equation, the Galerkin projection method, which uses the above-introduced RBF system as weight functions, is applied. Further, to the obtained function $\phi(x)$ the marching cubes algorithm constructing a new polygonal approximation of an isosurface is applied.

Rarefying polygonal grids is performed according to the following algorithm.

For each triangle of a grid the parameter $\chi$ characterizing the quality of a triangle is computed according to one of the following formulas:

$$\chi = \frac{l_{min}}{\rho},$$

where $l_{min}$ is the minimal side of a triangle, $\rho$ is a radius of inscribed into the triangle circumference;

$$\chi = \frac{\rho_1}{\rho_2},$$

where $\rho_1$ is a radius of circumscribed circumference, $\rho_2$ is a radius of inscribed circumference;

$$\chi = \frac{l_{min}}{l_{max}},$$

where $l_{min}$ is the length of the smallest side of a triangle, $l_{max}$ is the length of the greatest side of a triangle.

Further, for each triangle the parameter $\bar{\chi}$ is computed according to the formula:

$$\bar{\chi}=a_1 \cdot \chi + a_2 \cdot S_\Delta,$$

where $S_\Delta$ is the area of a triangle, $a_1$, $a_2$ are numerical coefficients which are chosen depending on the formula used for computing $\chi$ and on the required quality of a grid.

Afterwards, for each node of a grid the weight $\omega$ is calculated as arithmetical mean of values of $\bar{\chi}_i$ parameters for N triangles for which this node of a grid is vertex:

$$\omega = \frac{\sum_{i=1}^{N} \bar{\chi}_i}{N}.$$

Then, a node with the lowest weight $\omega$ is removed, a hole formed is triangulated, and changed weights of nodes of a grid are re-counted. This procedure is repeated until the quantity of triangles in a grid would meet the given one.

At the next step, a coefficient of specific electroconductivity of biological tissues is determined for every anatomical structure of the chest.

Values of specific electroconductivity for main types of chest tissues are given below (Hofer M. Computer tomography teaching manual [Russian translation]. Moscow: Meditsinskaya literatura, 2006; Martirosov E. G., Nikolaev D. V., Rudnev S. G. Technologies and methods for determination of human body composition. [In Russian].—Moscow: Nauka, 2006).

TABLE I

| Type of a tissue | Averaged specific electroconductivity, S/m |
|---|---|
| Liquor | 1.53000 |
| Blood | 0.67000 |
| Skeletal muscles | 0.33000 |
| Adipose tissue | 0.06700 |
| Liver | 0.25000 |
| Skin | 0.18000 |
| Lungs (at breath) | 0.04300 |
| Bone tissue, sponge | 0.00670 |
| Bone tissue, compact | 0.00025 |

Figure 10:
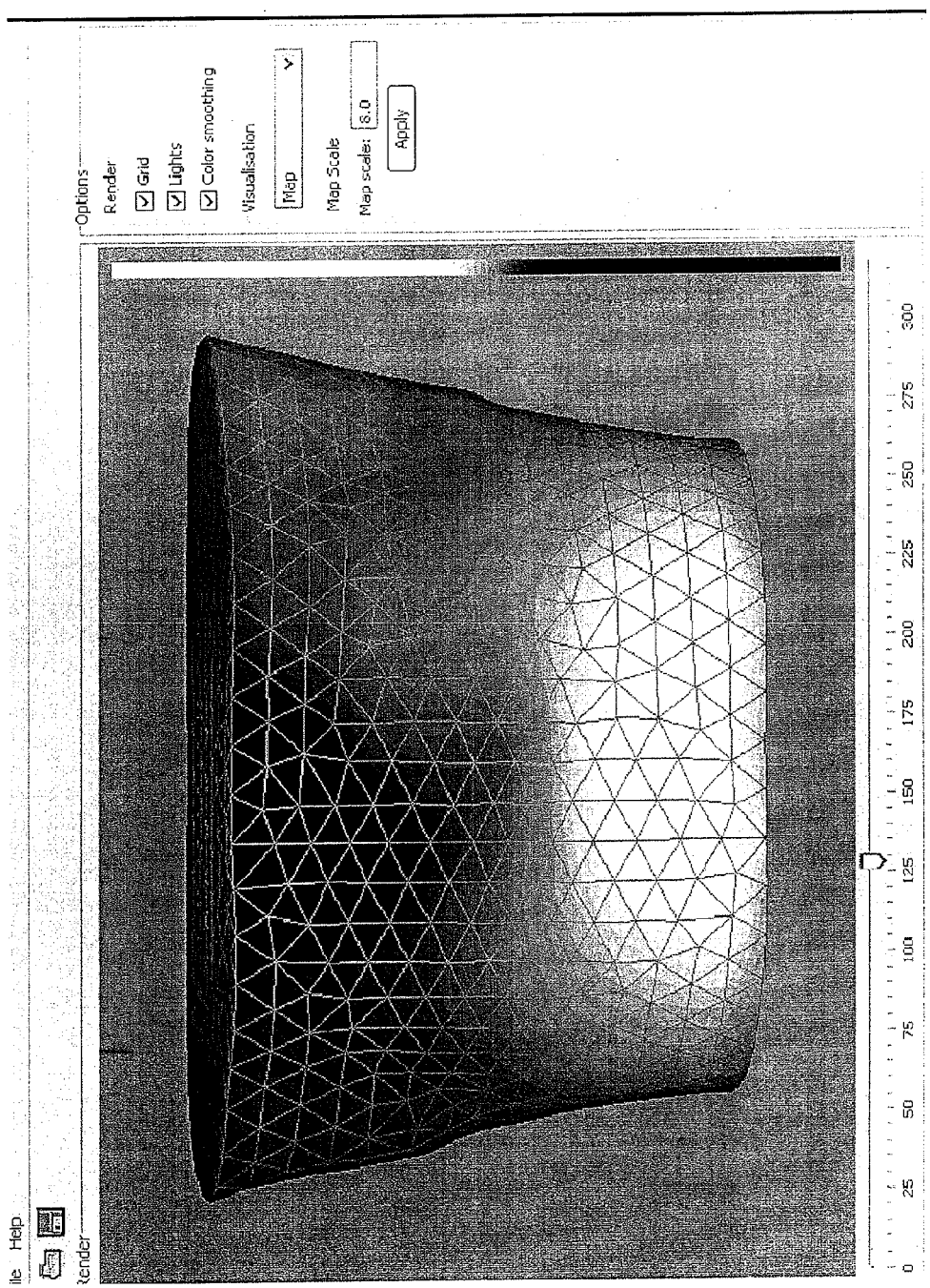
FIG. 10 presents isopotential maps on the torso surface.

FIG. 10 illustrates constructing isopotential maps on the torso surface.

Constructing isopotential maps is carried out by surface interpolation of ECG-signal values at each discrete moment with using radial basis functions.

The electric field potential on the chest surface S is represented as a decomposition by a system of radial basis functions (RBF):

$$U(x) = \sum a_j f_j(x), x \in S,$$

where $U(x)$ is the electric field potential, $f_i(x)$ are radial basis functions, $a_i$ are indefinite coefficients.

As RBF, functions of the following kind given at points of ECG-registration are used:

$$f_j(x) = \exp\left(-\frac{\|x - x_j\|}{c^2}\right)$$

where x is a random point on the body surface, $x_j$ are points of ECG-registration, $\|x-x_j\|$ is the smallest length of a line belonging to the surface S and connecting points x and $x_j$, c is an experimentally chosen coefficient that determines approximation properties of the function.

Coefficients $a_j$ are found from the condition for the minimum of functional J:

$$J = \frac{1}{2} \sum_{i=1}^{N} \left[\left(\sum_{j=1}^{N} a_j f_j(x_i) + a_0\right) - U(x_i)\right]^2$$

provided that $$\sum_{j=0}^{N} a_j = 0$$

where $U(x_i)$ are values of the electric field potential at x, points of ECG-registration on the chest surface, N is a number of points of ECG-registration.

For finding coefficients $a_j$, the corresponding system of linear algebraic equations (SLAE) with a matrix of N×N size is solved.

Potential $U(x_i)$ is calculated in nodes of the torso triangulation surface x, according to the formula:

$$U(x_i) = \sum_{j=1}^{N} a_j f_j(x_i) + a_0.$$

To calculate the potential at each point of the torso surface, a bilinear interpolation on values in vertices of a grid triangle, which this point belongs to, is applied.

The claimed method includes a method for noninvasive reconstructing the electric field potential of the heart at internal points of the chest on measured values of the electric field potential on the chest surface by a numerical solution of the inverse problem of electrocardiography for a model of the chest with a piecewise-constant coefficient of electroconductivity by the finite element method on the basis of iteration algorithms.

As an example of realizing the method, let us use a model of the chest in which a low electroconductivity of lungs is taking into account. Let $\Omega \in R^3$ be a part of the chest bounded by a sufficiently smooth border $\partial\Omega$, which includes the torso surface contacting with external medium $\Gamma_0$, cross-sections of the chest at the level of the diaphragm and clavicles $\Gamma_{T1}$ and $\Gamma_{T2}$ as well as the heart's epicardial surface $\Gamma_E$. Let us also introduce a surface $\Gamma_3$ consisting of surfaces $\Gamma_{T1}, \Gamma_{T2}$ and $\Gamma_E$: $\Gamma_3 = \Gamma_3 = \Gamma_{T1} \cup \Gamma_{T2} \cup \Gamma_E$; let us designate: $\overline{\Omega} = \Omega \cup \partial\Omega$.

Figure 11:
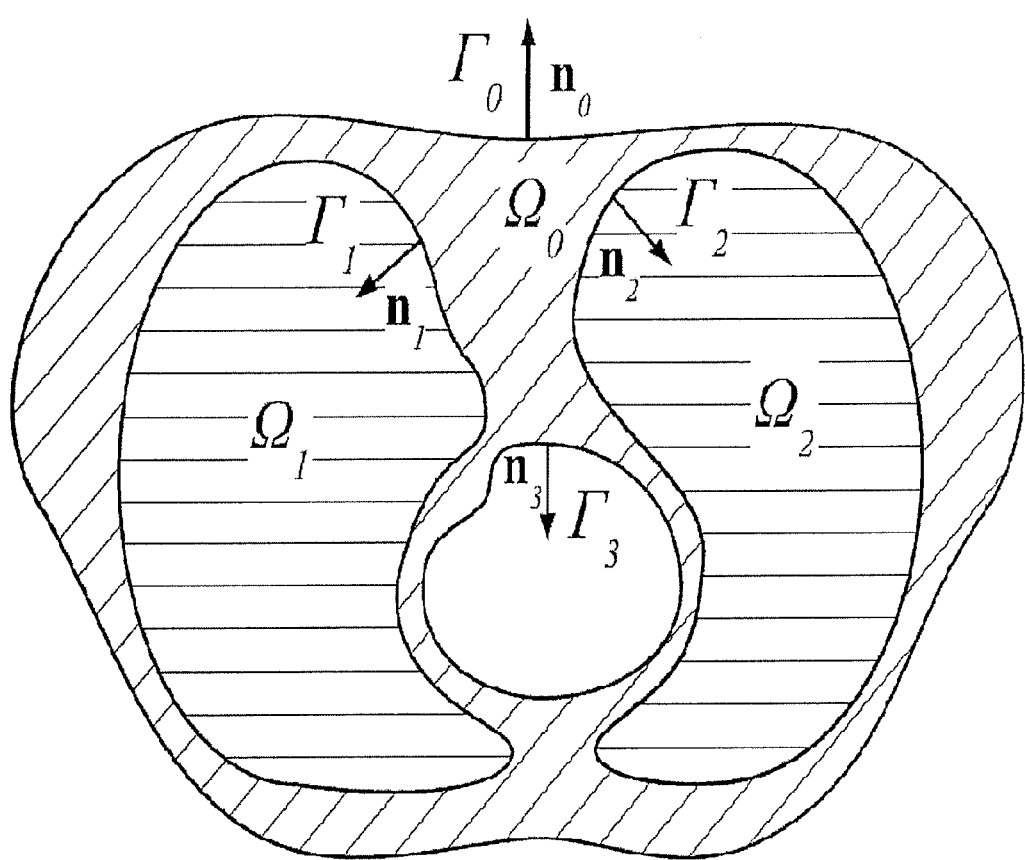
FIG. 11 illustrates geometrical ratios of the chest, which are used in the boundary element method.

In domain $\Omega$ let us distinguish two sub-domains $\Omega_1$ and $\Omega_2$ with sufficiently smooth borders $\Gamma_1$ and $\Gamma_2$ which correspond to right and left lungs. Let us also distinguish a sub-domain $\Omega_0 = \Omega \setminus (\Omega_1 \cup \Omega_2)$ representing a space of the chest between its external surface and the heart not occupied by lungs. In every of domains $\Omega_0, \Omega_1, \Omega_2$ biological tissues have specific electroconductivity $k_0, k_1, k_2$. Coefficients $k_1$ and $k_2$ correspond to electroconductivity of right and left lungs, $k_1 = k_2$. Coefficient $k_0$ corresponds to an averaged value of electroconductivity of chest tissues without lungs. Geometrical ratios indicated are presented in FIG. 11.

The electric field potential of the heart in every of domains $\Omega_i$, i=0, 1, 2 is assumed to satisfy the Laplace equation:

$$\Delta u(x) = 0, \quad (1)$$

where $x = (x_1, x_2, x_3)^T \in \Omega_i \subset R^3$ is a point in a three-dimensional space, $$\Delta \equiv \left(\frac{\partial^2}{\partial x_1^2} + \frac{\partial^2}{\partial x_2^2} + \frac{\partial}{\partial x_3^2}\right)$$

is the Laplace operator in $R^3$.

At the part of borders $\Gamma_0$ of domain $\Omega$, the Dirichlet condition (electric field potential measured as a result of surface ECG mapping) is considered to be known:

$$u(x) = U(x), x \in \Gamma_0 \quad (2)$$

The Dirichlet condition contains a noise component as a result of experimental measurements:

$$U(x) = u_0(x) + \xi(x), x \in \Gamma_0, x \in \Gamma_0 \quad (3)$$

where $u_0(x)$ is the exact value of a potential on the chest surface, $\xi(x)$ is a measurement error estimated as $\|\xi(x)\|_{L_2} < \delta$.

At the same part of borders, the Neumann condition is also known:

$$\frac{\partial u(x)}{\partial n} = P(x) = 0, x \in \Gamma_0 \quad (4)$$

where $$\frac{\partial u(x)}{\partial n}$$

is a potential derivative $u(x)$ along the internal normal to the surface.

At interfaces of media with a different electroconductivity $\Gamma_i$, i=1, 2, 3, conditions of continuity of potential and current are valid:

$$u_0(x) = u_i(x) \quad (5)$$
$$k_i \cdot \frac{\partial u_0(x)}{\partial n} = k_0 \frac{\partial u_i(x)}{\partial n}, i = 1, 2, 3$$

The inverse problem of electrocardiography consists in the following: it is required to find such function $u(x)$, which in each of domains $\Omega_i$, i=0, 1, 2 would satisfy the Laplace equation (1), at the border $\Gamma_0$—to boundary conditions (2), (4), and at borders $\Gamma_i$, i=1, 2, 3—to conditions (5).

This problem to be stated is known as the Cauchy problem for the Laplace equation in a piecewise-homogeneous medium.

For solving the inverse problem of electrocardiography the boundary element method is used (Brebbia C., Telles J., Wrobel L. Boundary element methods [Russian translation]. Moscow: Mir, 1987).

External surfaces of the chest and heart and surfaces of lungs are approximately substituted by a boundary-element grid—a polygonal surface consisting of $2 \cdot 10^3$-$5 \cdot 10^3$ planar triangles. Each of surfaces $\Gamma_i$ is split into $N_i$ boundary elements $\omega_j$: $\Gamma_i = \cup_{j=1}^{M_i} \omega_j$. The potential u(s) and its normal derivative q(s) on surfaces $\Gamma_i$ are represented in the form of decomposition according to the system of linearly independent finite basis functions $\phi_j(s)$:

$$u(s) = \sum_{i=1}^{N} u_j \cdot \varphi_j(s), \quad (6)$$

$$q(s) = \sum_{i=1}^{N} q_j \cdot \varphi_j(s),$$

where coefficients of decomposition $u_j$ and $q_j$ are values of the potential u(s) and its normal derivative q(s) in nodes of a boundary-element grid.

As a result, four vectors $u_0$, $u_1$, $u_2$, $u_3$ and four vectors $q_0$, $q_1$, $q_2$, $q_3$ corresponding to values of the potential and its normal derivative on surfaces $\Gamma_0$, $\Gamma_1$, $\Gamma_2$, $\Gamma_3$ are formed. Of these vectors only two ones $u_0$ and $q_0$ are known from boundary conditions (2), (4):

$$u_0 = U_0, q_0 = 0 \quad (7)$$

The direct boundary element method directly uses the Green's third (main) formula that connects values of the potential and its normal derivative on boundary surfaces $\Gamma$ to values of the potential within a computational domain $\Omega$ in the form of integral relationship:

$$2\pi u(x) = \int_\Gamma q(y) \cdot \frac{1}{|x-y|} ds - \int_\Gamma u(y) \cdot \frac{\partial}{\partial n_y} \frac{1}{|x-y|} ds, \quad (8)$$

$$x \in \Gamma, y \in \Gamma,$$

where $x=(x_1, x_2, x_3)^T$ is a fixed point and $y=(y_1, y_2, y_3)^T$ is a «sliding» one on the surface $\Gamma$, $|x-y| \equiv \sqrt{(x_1-y_1)^2+(x_2-y_2)^2+(x_3-y_3)^2}$ is the Euclidean distance between points x and y, $$q(y) \equiv \frac{\partial}{\partial n_y} u(y)$$

is a normal derivative of the potential at point y, $$\frac{\partial}{\partial n_y}$$

is a differentiation operator along the direction of an unit normal vector to the surface $\Gamma$ at point $y \in \Gamma$, ds is a differential element of the surface $\Gamma$.

Using the Green's third formula for points laying on surfaces $\Gamma_i$ yields a system of the Fredholm integral equations (of $1^{st}$ and $2^{nd}$ kinds). After boundary-element discretization of functions u(s) and q(s) according to formulas (8) and и transformations taking into account conditions (5) and (7), this system of integral equations is written as a system of four matrix-vector equations with four unknown vectors $u_1$, $u_2$, $u_3$ and $q_3$:

$$-G_{03} \cdot q_3 + R_{01} \cdot u_1 + R^{02} \cdot u_2 + H_{03} \cdot u_3 = c_0$$

$$-G_{13} \cdot q_3 + R_{11} \cdot u_1 + R_{12} \cdot u_2 + H_{13} \cdot u_3 = c_1$$

$$-G_{23} \cdot q_3 + R_{21} \cdot u_1 + R_{22} \cdot u_2 + H_{23} \cdot u_3 = c_2$$

$$-G_{33} \cdot q_3 + R_{31} \cdot u_1 + R_{32} \cdot u_2 + H_{33} \cdot u_3 = c_3 \quad (9)$$

The following designations are used here:

$G_{ij}$ are matrices obtained as a result of discretization of integrals of the following kind:

$$\int_{\Gamma_j} \frac{1}{|x-y|} ds_y, x \in \Gamma_i, y \in \Gamma_j,$$

$H_{ij}$ are matrices obtained as a result of a discretization of integrals of the following kind:

$$\int_{\Gamma_y} \frac{\partial}{\partial n_y} \frac{1}{|x-y|} ds_y, x \in \Gamma_i, y \in \Gamma_j,$$

E—is an unit matrix, $R_{ij}$ are matrices with a structure $$R_{ij} = \overline{H}_{ij} - \frac{k_0}{k_j} G_{ij} \cdot G_{ij}^{-1} \cdot \hat{H}_{jj}$$

where:

$\overline{H}_{ij} = H_{ij}, i \neq j, \hat{H}_{ij} = H_{ij}, i \neq j,$ $\overline{H}_{ij} = H_{ij} + 2\pi E, i = j' \hat{H}_{ij} = H_{ij} - 2\pi E, i = j'$ $c_i$ are known vectors of the following kind: $c_i = -\overline{H}_{i0} \cdot U_0$.

For solving a system of matrix-vector equations the following iteration algorithm being an analogue of the Seydel method for solution of systems of linear algebraic equations is used:

$$q_3^{(0)} = f_1, u_1^{(0)} = f_2, u_2^{(0)} = f_3, u_3^{(0)} = f_4 \quad (10)$$

$$G_{03} \cdot q_3^{(k+1)} = -c_0 + R_{01} \cdot u_1^{(k)} + R_{02} \cdot u_2^{(k)} + H_{03} \cdot u_3^{(k)} \quad (11)$$

$$R_{11} \cdot u_1^{(k+1)} = c_1 + G_{13} \cdot q_3^{(k+1)} - R_{12} \cdot u_2^{(k)} - H_{13} \cdot u_3^{(k)} \quad (12)$$

$$R_{22} \cdot u_2^{(k+1)} = c_2 + G_{23} \cdot q_3^{(k+1)} - R_{21} \cdot u_1^{(k+1)} - H_{23} \cdot u_3^{(k)} \quad (13)$$

$$H_{33} \cdot u_3^{(k+1)} = c_3 + G_{33} \cdot q_3^{(k+1)} - R_{31} \cdot u_1^{(k+1)} - R_{32} \cdot u_3^{(k+1)} \quad (14)$$

where $f_1$, $f_2$, $f_3$, $f_4$ are randomly given vectors of an initial approximation, k=1, 2, . . . , n are iteration numbers.

To determine a number of iterations, the principle of the residual (the Morozov principle) is applied: a procedure is stopped at the iteration k starting with that the norm according to first equation of the residual does not exceed an absolute error of the free term:

$$\|-G_{03} \cdot q_2^{(k)} + R_{01} \cdot u_1^{(k)} + R_{02} \cdot u_2^{(k)} + H_{03} \cdot u_3^{(k)} - c_0\| \leq \|H_{00}\| \cdot \|\delta\| \quad (15)$$

where $\delta$ is an absolute error of determination of the electric field potential on the chest surface, $\|\ldots\|$ is the Euclidean vector norm.

Solution of matrix-vector equations (12), (13), (14) at each step of an iteration procedure is realized on the basis of standard algorithms of computational linear algebra (LU-decomposition, QR-decomposition, etc.).

Solution of the matrix-vector equation (11) at each step of an iteration procedure is computed on the basis of the Tikhonov regularization method: a regularizing solution $q_3^{(k)}$ depending on a regularization parameter $\alpha$ is found as a solution of the next matrix-vector equation:

$$(G_{03})^T \cdot (G_{03} + \alpha \cdot E) \cdot q_3^{(k+1)} = (G_{03})^T \cdot (-c_0 + R_{01} \cdot u_1^{(k)} + R_{02} \cdot u_2^{(k)} + H_{03} \cdot u_3^{(k)}) \quad (16)$$

where $(G_{03})^T$ is a matrix transponated regarding the matrix $G_{03}$, E is an unit matrix.

A regularization parameter $\alpha$ (a positive real number) is computed according to the formula:

$$\alpha = \alpha_0 + \beta \cdot p^{-(k)}, \quad (17)$$

where $\alpha_0$ is a small real parameter depending on an error of defining boundary conditions of the inverse problem of electrocardiography, p is a positive real parameter depending on the convergence velocity of an iteration procedure, $\beta$ is a positive real parameter depending on the accuracy of an initial approximation in an iteration procedure, k is the iteration number.

Figure 12:
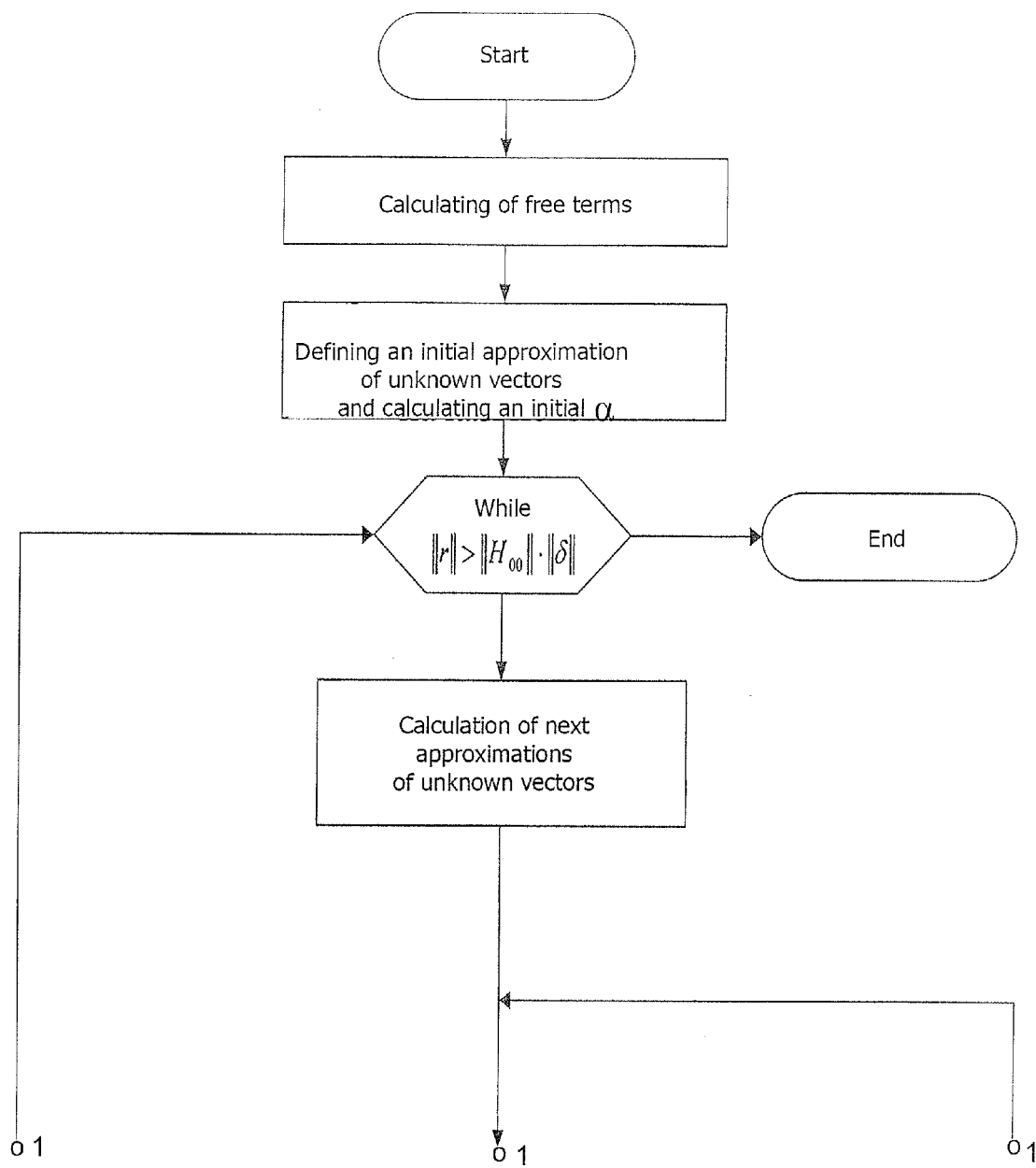
FIG. 12 is a block-diagram of a computational algorithm of solution of the inverse problem of electrocardiography based on an iteration algorithm.
Figure 12:
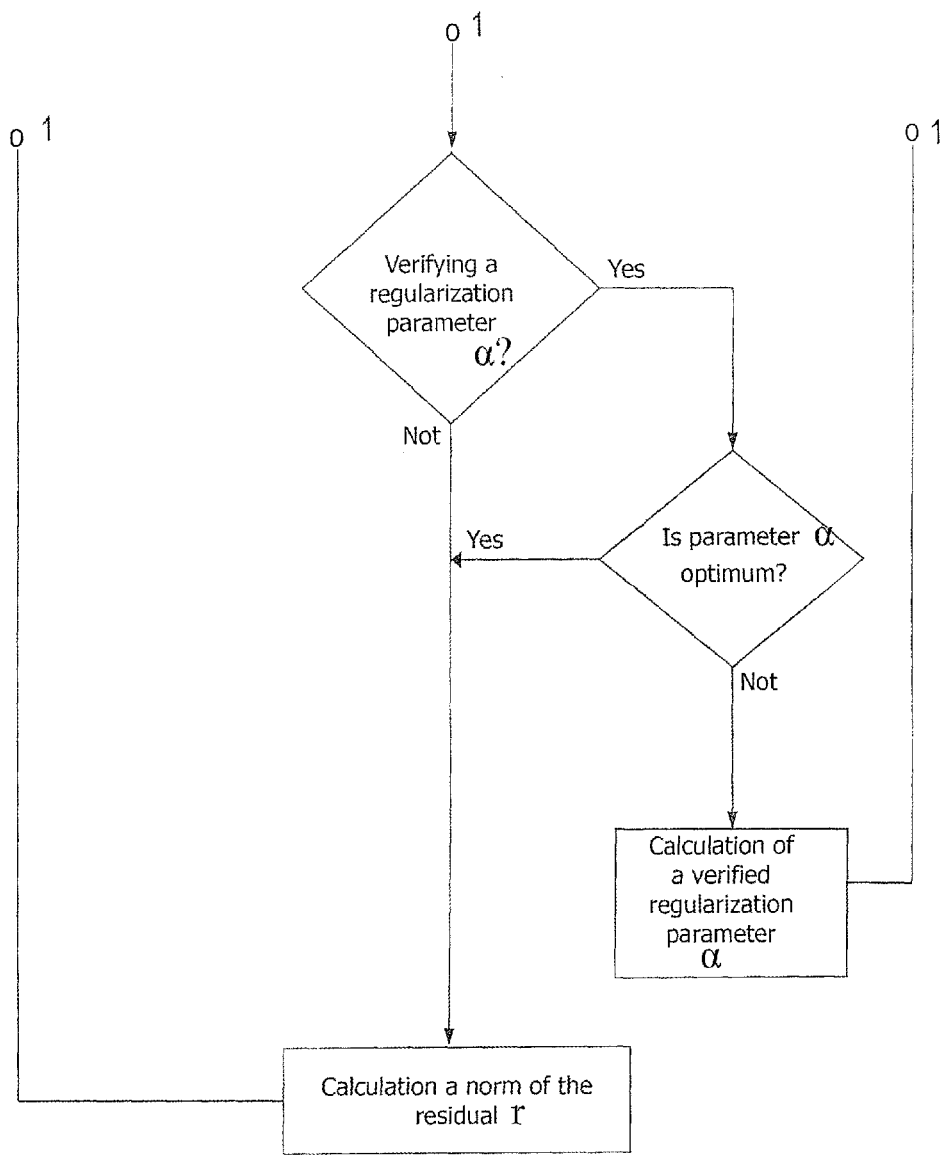

A block-diagram of the algorithm is shown in FIG. 12.

Figure 13:
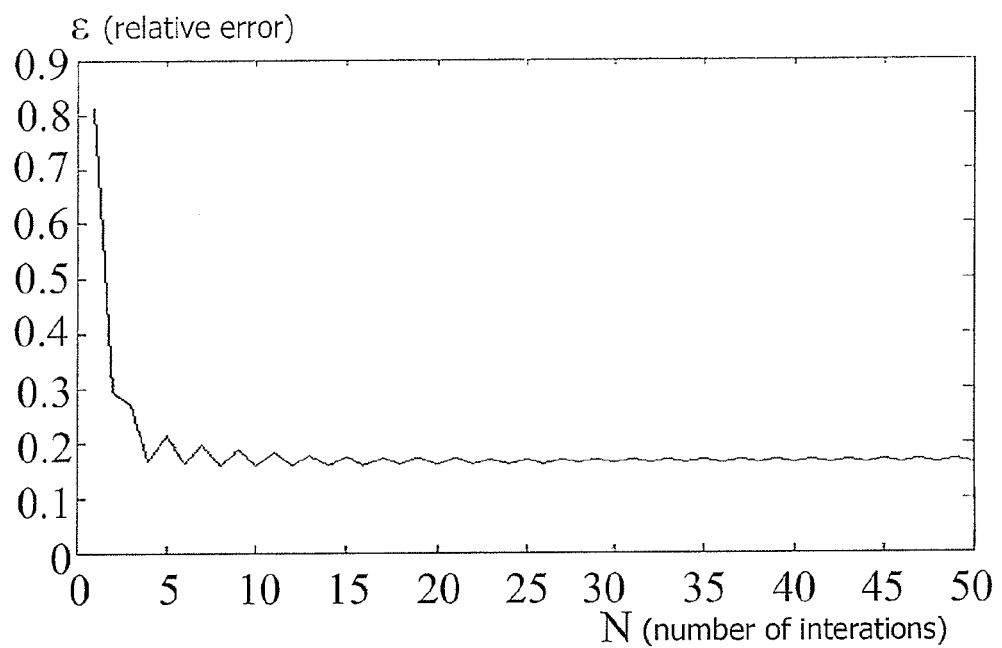
FIG. 13 shows convergence diagrams of an iteration algorithm with using the Tikhonov regularization. In upper drawing an algorithm convergence is shown without verifying a regularization parameter α at each step of an iterative procedure. In lower drawing an algorithm convergence is shown with verifying a regularization parameter α at each step of an iterative procedure.
Figure 13:
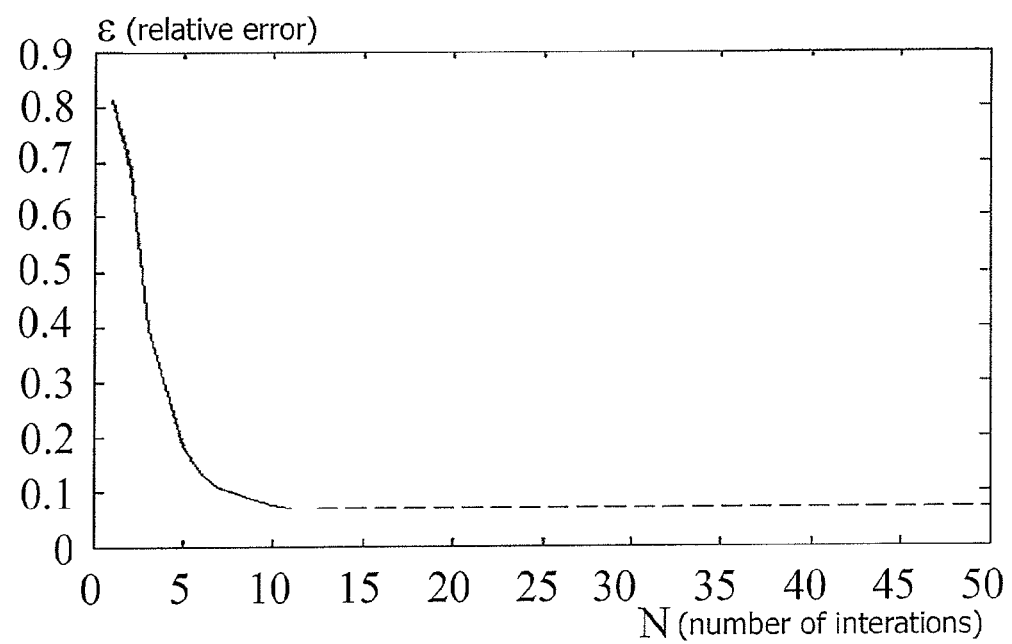

FIG. 13 depicts convergence diagrams of an iteration procedure with a constant regularization parameter $\alpha$ (12A) and with verifying this parameter at each step of iteration $\alpha$ according to the afore-given formula (FIG. 12B). The following parameters were used: $\alpha_0 = 10^{-7}$, $\beta = 10^2$, $p = 3.0$.

For calculations a model of the torso, heart and lungs of a real patient was used. The total number of triangle elements in a grid for the torso, heart and lungs was 3200. For modeling the standard electric field of the heart, a quadruple source to be placed in a geometrical center of the heart was used. Specific electroconductivity of lungs was assumed to be equal to 0.04300 S/m (lungs at breathe), averaged electroconductivity of chest tissues without lungs was assumed to be equal to 0.22 S/m.

Figures 14A, 14B:
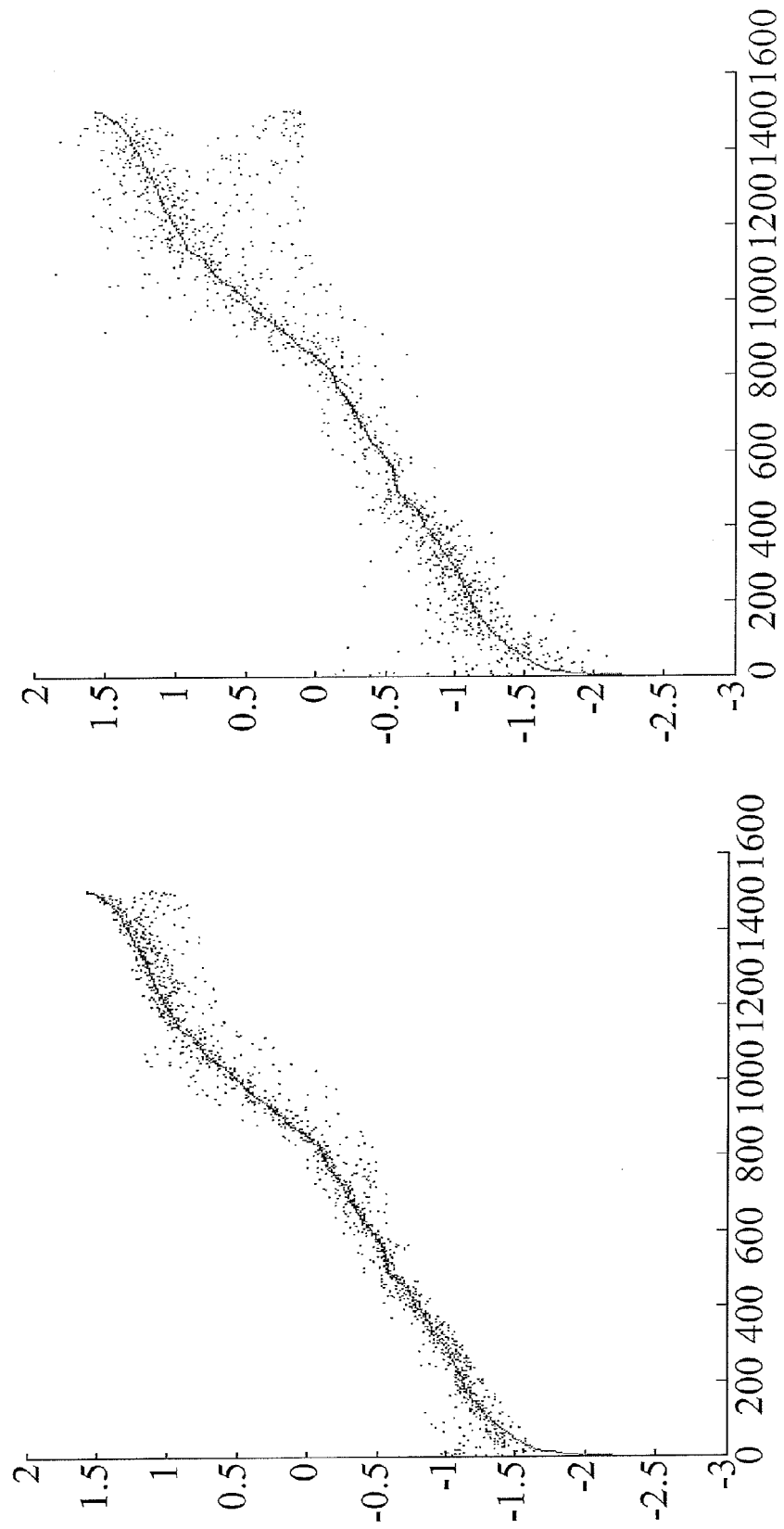
FIG. 14 depicts diagrams of errors of reconstructing the electric field for homogeneous and piecewise-homogeneous models of the chest in comparison with exact data.

FIG. 14A shows diagrams of the standard potential and a potential reconstructed by an algorithm disclosed in the present invention for a piecewise-homogeneous model of the chest. FIG. 14B shows diagrams of the standard potential and a potential reconstructed for a model of homogeneous medium. The same algorithm was used but electroconductivity of lungs was assumed to be equal to an averaged electroconductivity of chest tissues. The abscissas axis represents an index number of a boundary-element node; the ordinates axis represents a value of the potential in a corresponding node. Nodes were put in proper order in accordance with exact values of the potential in given node. The exact value of the potential is marked by red and a reconstructed value of the potential is marked by blue.

Figure 15A:
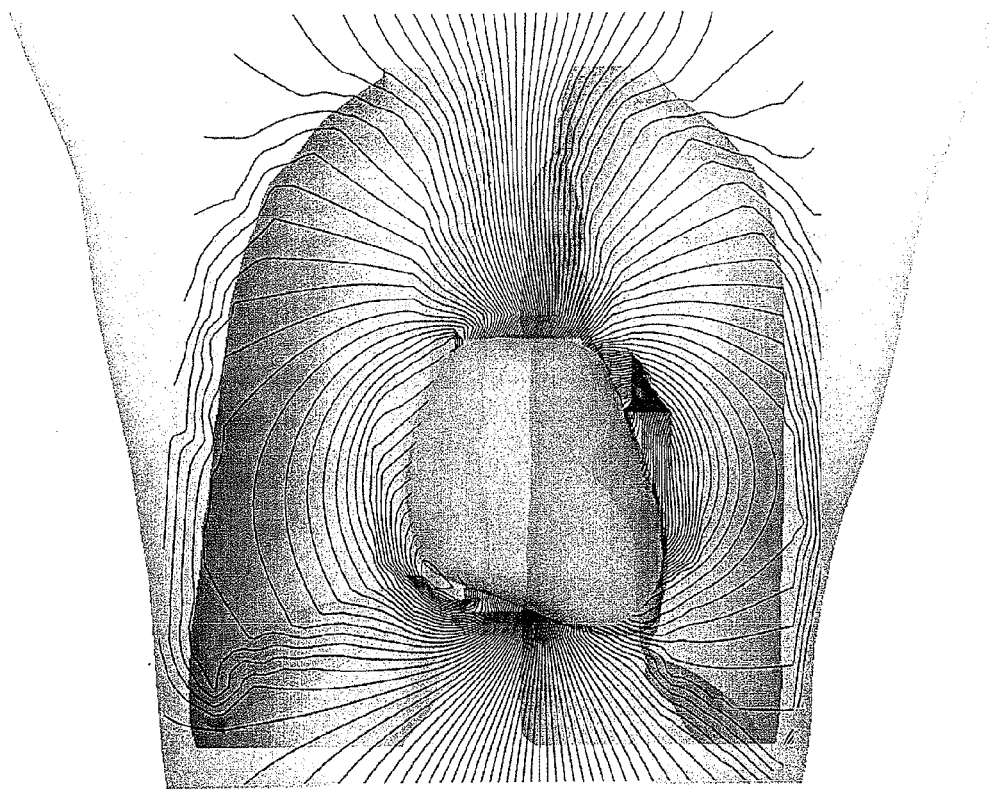
FIG. 15 shows isopotential maps of a reconstructed electric field of the heart for a piecewise-homogeneous model of the chest on cross and frontal sections of the torso.
Figure 15B:
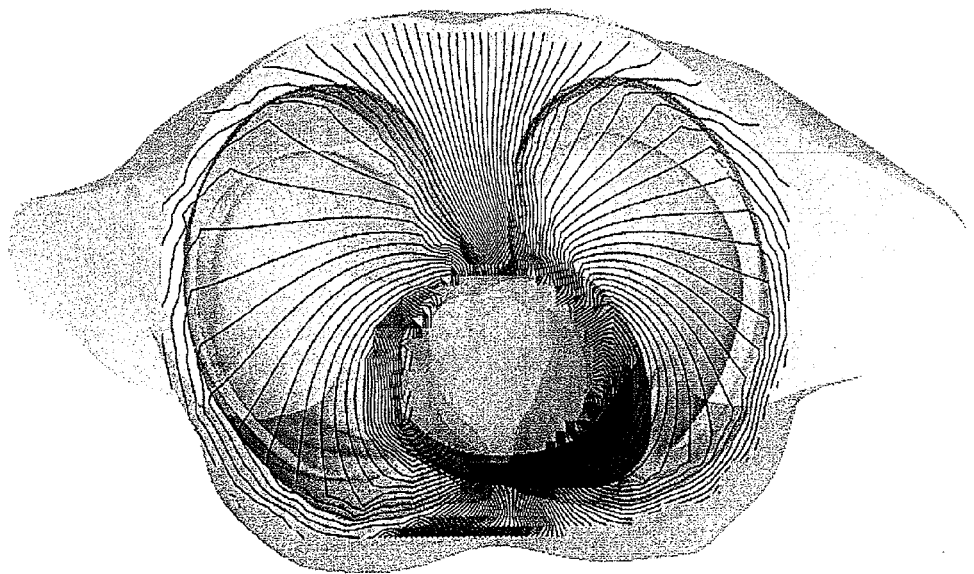
Figure 16C:
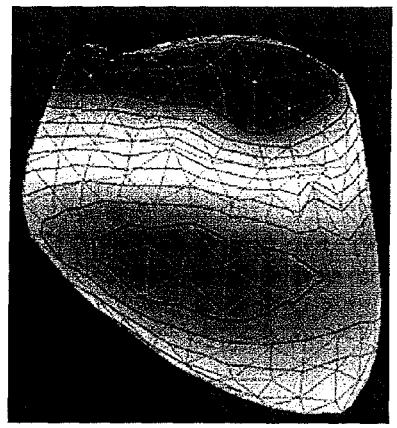
FIG. 16 presents results of reconstructing the electric field on the heart surface for homogeneous and inhomogeneous models of the chest in comparison with exact data.
Figure 16B:
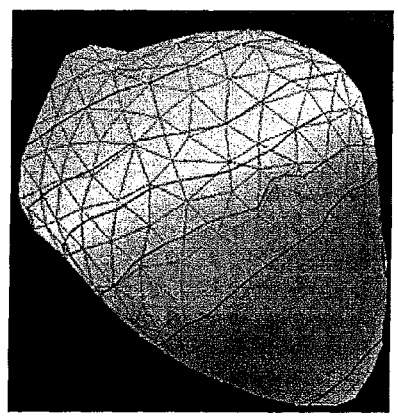
Figure 16A:
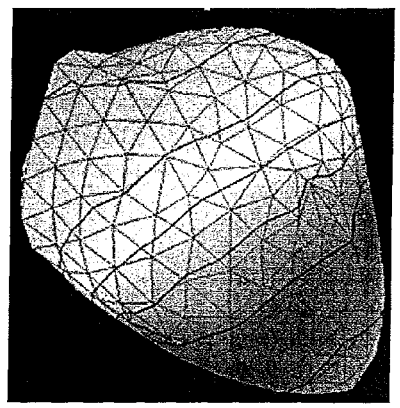

FIG. 15 depicts a distribution of isopotential lines in cross- and frontal sections of the torso for a piecewise-homogeneous model of the chest. FIG. 16 shows imposed on realistic models of the heart isopotential maps of the exact electric potential (16A) calculated by an algorithm disclosed in the present invention for a piecewise-homogeneous model of the chest (16B) and of a reconstructed one by the same algorithm for a homogeneous model of the chest (16C). The upper row is a front view, the lower row—a view from behind.

The method includes an iteration method for solving a system of matrix-vector equations (10-14); in this method at each step an equation (11) is solved with using a pseudo-inversion of a matrix on the basis of SVD-decomposition with filtrating singular numbers to be small on module.

The regularizing solution of the matrix-vector equation (11), $q_2^{(k+1)}$, depending on a parameter $\epsilon$ is found according to the formula:

$$q_3^{k+1} = (G_{03})_\epsilon^+ (-c_0 + R_{01} \cdot u_1^{(k)} + R_{02} \cdot u_2^{(k)} + H_{03} \cdot u_3^{(k)}),$$

where $(G_{03})_\epsilon^+$ is a regularized pseudo-inverse matrix depending on a parameter $\epsilon$.

This matrix $(G_{03})_\epsilon^+$ is computed as follows. Matrix $G_{03}$ of M×N size is represented in the form of SVD-decomposition: $G_{03} = U\Sigma V^T$ where U is an orthogonal matrix of M×M size, V is an orthogonal matrix of N×N size, E is a diagonal matrix of M×N size in whose main diagonal singular numbers of matrix $G_{03}$ are arranged in diminishing order; remained elements are equal to zero. Computing SVD-decomposition of matrix $G_{03}$ is performed by one of standard algorithms of computational linear algebra (QL-algorithm, QR-algorithm, etc.).

All the non-zero singular numbers $\sigma_j$ of matrix $\Sigma$, for which the condition $\sigma_j < \epsilon$ is valid, are substituted by zeroes. Further, a regularized pseudo-inverse matrix $\Sigma^+$ is constructed: non-zero diagonal elements $\sigma_j$ of matrix $\Sigma$ are conferred by meanings $$\frac{1}{\sigma_j}.$$

Then, a regularized pseudo-inverse matrix $(G_{03})_\epsilon^+$ depending on a parameter $\epsilon$ is constructed according to the formula:

$$(G_{03})^+ = V\Sigma^+ U^T.$$

Parameters $\epsilon$ that plays the role of a regularization parameter is determined according to the formula:

$\epsilon = \epsilon_0 + \beta \cdot p^{-(k)}$ where $\epsilon_0$ is a small real parameter depending on an error of defining boundary conditions of the inverse problem of electrocardiography, p is a positive real parameter depending on the convergence velocity of an iteration procedure, $\beta$ is a positive real parameter depending on the accuracy of an initial approximation in an iteration procedure, k is the iteration number.

The method comprises an iteration method for solving the system of matrix-vector equations under consideration (10)-(14); in this method at each step the equation (11) is solved by an iteration method based on generalized minimal residual (GMRes) algorithm.

The description of GMRes-algorithm used in the present invention, see Saad Y. Iterative Methods for Sparse Linear Systems (2nd ed.), SIAM, Philadelphia 2003.

When solving the equation (11), iterations of GMRes-algorithm are stopped as soon as the following condition is fulfilled:

$$\|u^{(2k)} - u^{(2k-2)}\| < \epsilon_1$$

where $\|\ldots\|$ is the Euclidean norm of a vector, k is the iteration number, $\epsilon_1$ is a small parameter depending on the machine accuracy.

When solving SLAE (11), a number of iterations of GMRes-algorithm is determined according to the formula:

$$n = n_0 + \lambda \cdot k$$

where n is a number of iterations of GMRes-algorithm, k is the iteration number in a procedure (10)-(14), $n_0$ and $\lambda$ are positive whole numbers depending on the accuracy of an initial approximation and on the convergence velocity of a procedure (11)-(13).

The method includes an iteration method for solving matrix-vector equations (10)-(14) with matrices of high size; in this method at each step of an iteration procedure these equations are solved on the basis of the fast multipole method.

For solving matrix-vector equations (10)-(14), at each step of an iteration procedure an iterative method including only operations of matrix-vector addition (subtraction) and multiplication is used, for example, generalized minimal residual (GMRes) algorithm.

Figure 17:
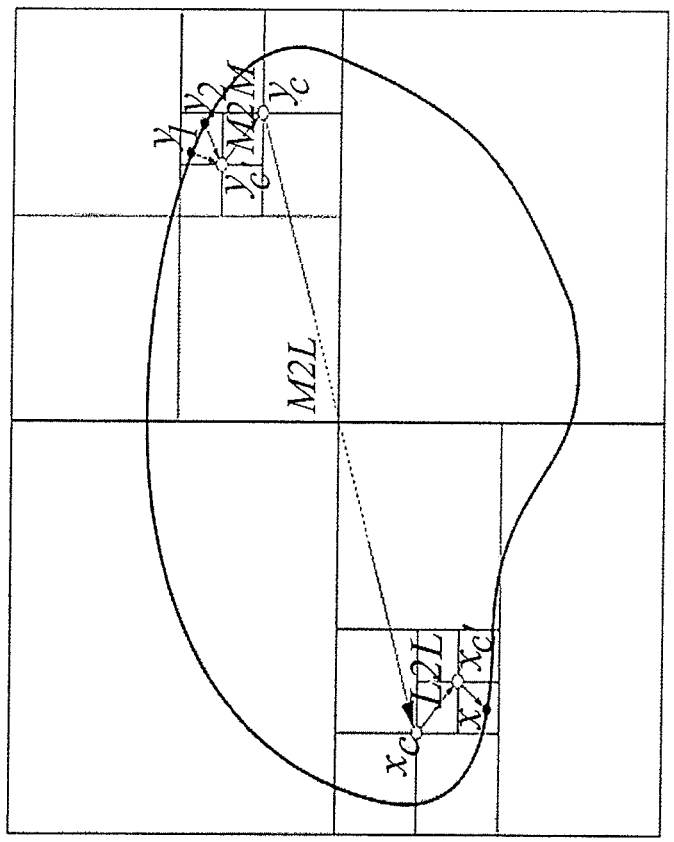
FIG. 17 illustrates the main principles of the "fast multipole method". In the left column from above a scheme of operations at realizing classical BEM is shown, from below—a scheme of operations for realizing FMM BEM. In the right column a scheme of a hierarchical space splitting and details of realizing the FMM BEM method are shown.
Figure 17:
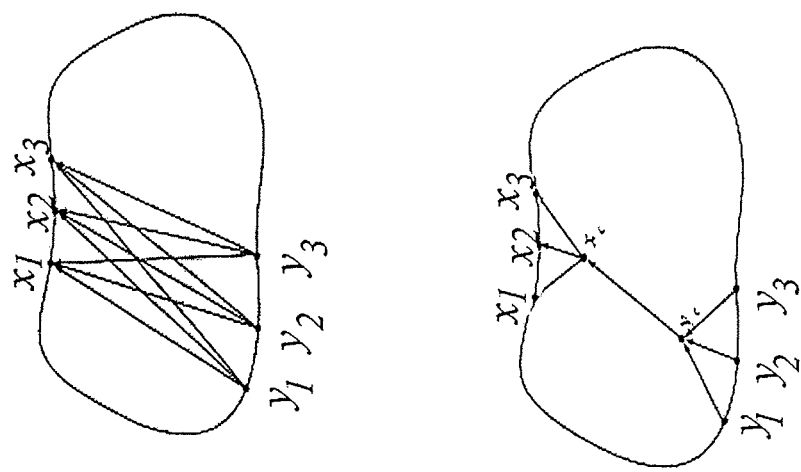
Figure 17:
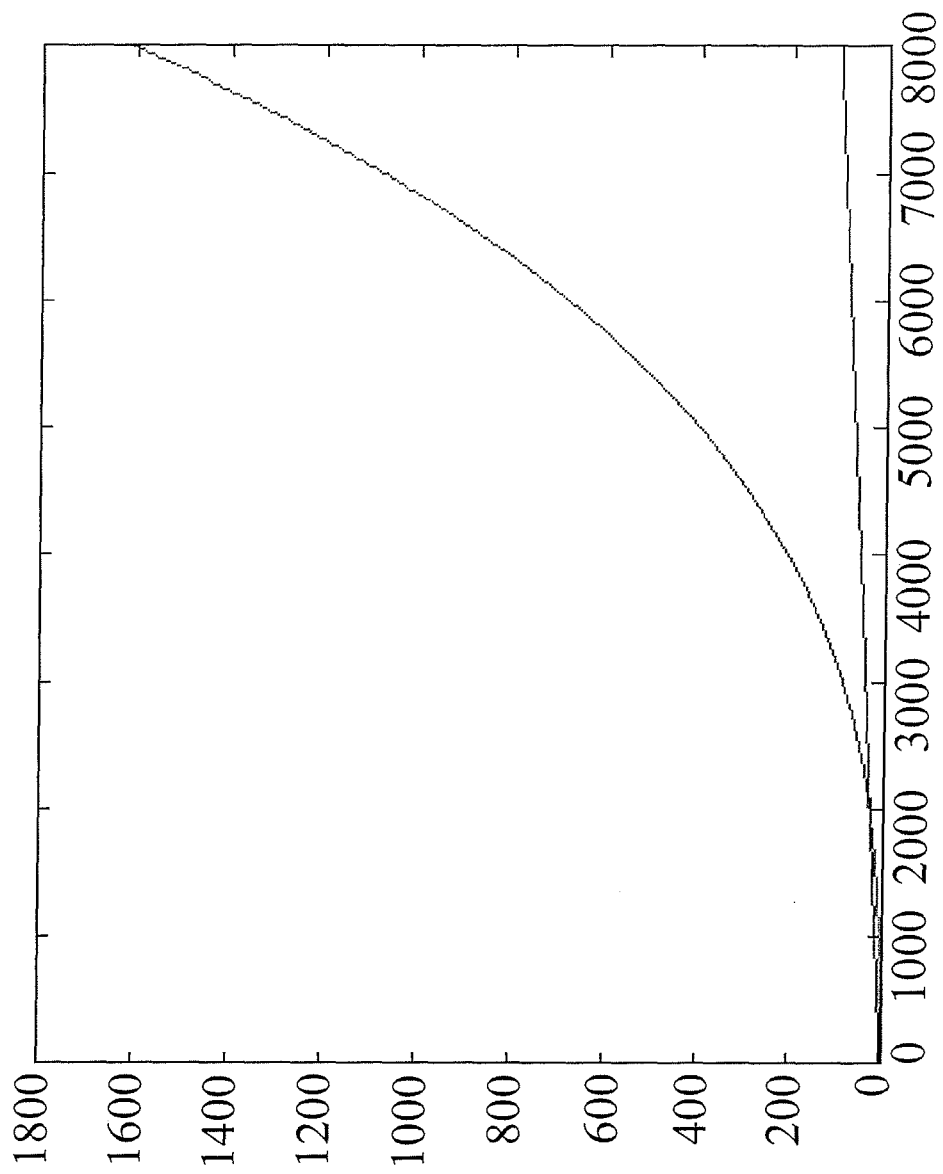

For realizing an operation of multiplication of matrix by vector, the fast multipole method presented in FIG. 17 is applied. Its detailed description, see Yoshida K. Applications of fast multipole method to boundary integral equation method. Ph.D. Dissertation, Department of Global Environment Engineering, Kyoto University, 2001). The main idea of this method is disclosed in FIG. 17.1.

Realizing the fast multipole method includes the following stages (FIG. 17.2):
1. A hierarchical splitting of computational domain $\Omega$ into sub-domains, i.e., constructing an oct-tree, is implemented.

Kernels of integrals:

$$\int_{\Gamma_j} \frac{1}{|x-y|} ds_y, x \in \Gamma_i, y \in \Gamma_j,$$

$$\int_{\Gamma_y} \frac{\partial}{\partial n_y} \frac{1}{|x-y|} ds_y, x \in \Gamma_i, y \in \Gamma_j,$$

whose discretization results in the formation of matrices $H_{ij}$ and $G_{ij}$, are divided on two variables—x and y—based on decomposition in series just as a system of spherical functions (multipole decomposition) regarding given nodes x, and y, in sub-domains of a hierarchical splitting of computational domain.
2. Multipole moments in leaves of oct-tree are computed on the basis of above-written multipole decomposition.
3. Multipole moments for parents' levels of oct-tree are computed on the basis of earlier computed multipole moments (M2M).
4. Values of functions at remote points are computed on the basis of earlier computed multipole moments (M2L, L2L).

A comparative diagram of the temporal complexity of the classical boundary element method and the fast multipole decomposition method is shown in FIG. 17.3.

Figure 18G:
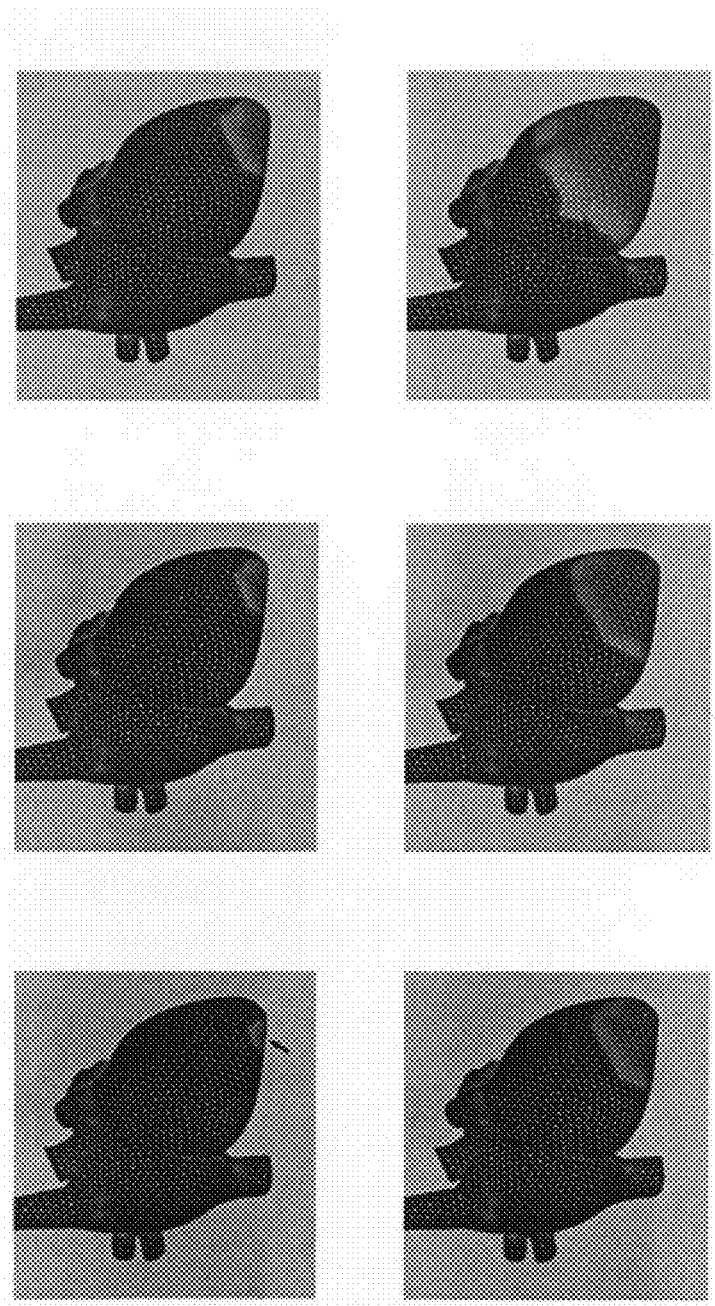
FIG. 18 shows examples of visualizing results of noninvasive electrophysiological study of the heart.

Examples of visualizing results of noninvasive electrophysiological study of the heart are presented in FIG. 18.

The following kinds of visual representation are used:
1. Constructing electrograms at interactively chosen points of the heart epicardial surface, endocardial surfaces of interventricular and interatrial septa, as well as at internal points of the chest on tomography cross-sections (FIG. 18A).
2. Constructing isopotential maps on tomography cross-sections of the chest (FIG. 18B).
3. Constructing isopotential and isochronous maps on the heart epicardial surface, endocardial surfaces of interventricular and interatrial septa (FIG. 18C).
4. Visualizing the dynamics of the myocardium excitation on the heart epicardial surface, endocardial surfaces of interventricular and interatrial septa in animation mode (propagation maps) (FIG. 18D).

Unipolar electrograms are constructed by interpolation of computed values of the heart electric field potential for all the moments of the cardiocycle at a given point. Bipolar electrograms are constructed as the difference of electrograms in the node chosen and at the point located in the vicinity to this node at a distance $\Delta l$ in the direction to l. Parameters $\Delta l$ and l are interactively given.

Isopotential maps are constructed on the basis of bilinear interpolation of computed values of the heart electric field potential in nodes of a grid at a given moment of the cardiocycle by a gradient painting method or by a method for constructing isopotential lines.

For constructing isochronous maps, two modes—manual and automatic—are provided. In manual mode in the interactively chosen node of a grid an unipolar electrogram U(t), a bipolar electrogram $U_b = U_1(t) - U_2(t)$ as well as a differential electrogram $$U^I(t) = \frac{dU(t)}{dt} -$$

the diagram of first derivative of an unipolar electrogram over time are reconstructed. An operator, in interactive mode, marks in diagrams indicated a time-point z corresponding to a start of the myocardium activation at a given point. In automatic mode, the choice of the corresponding time-point mark r proceeds without operator's interference. The time-point r is determined as a maximum of a negative differential unipolar electrogram:

$$\tau = \max\left(-\frac{dU(t)}{dt}\right).$$

Based on bilinear interpolation of $\tau$ values in nodes of a grid, isochronous maps are visualized by means of gradient painting or of constructing isochronous lines. The same data are represented in animation mode in the form of so-called propagation maps.

Figure 19:
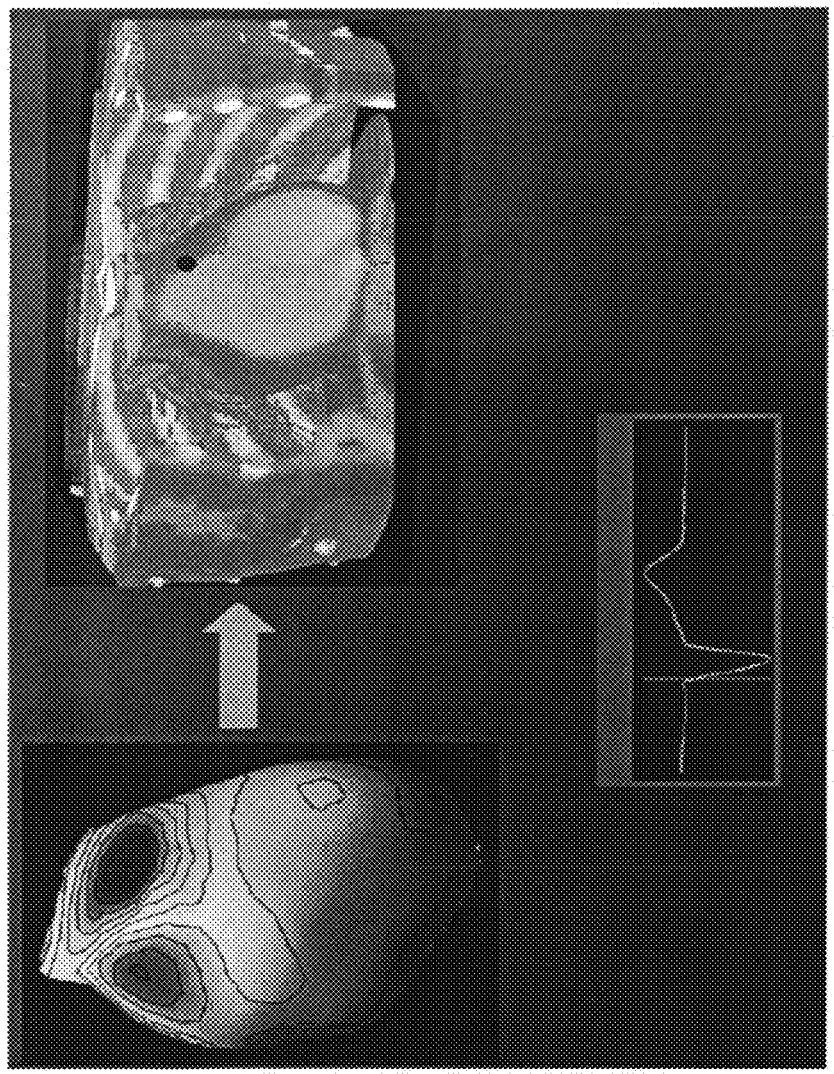
FIG. 19 presents an example of topical diagnosis of an arrhythmogenic source.

FIG. 19 presents reconstructed by the described method epicardial isochronous maps of the extrasystole caused by an ectopic source in the region of excretory tract of the right ventricle. The mini-circle indicates a localization of the ablation electrode with the help of which a successful radiofrequency ablation of this ectopic source was implemented.

What is claimed is:
1. A method of noninvasive electrophysiological study of the heart, comprising the following steps:
  attaching one-off registration electrodes a chest surface,
  ECG-registering in several unipolar leads from the chest surface:
    processing ECG-signals in a real-time mode,
    retrospective processing the ECG signals,
    generating a computer (CT) or magneto-resonance (MRT) tomography of the chest of a patient with the attached electrodes,
  constructing and editing computer voxel models of chest and heart organs,
  constructing polygonal models of a torso, the heart, lungs, and other organs of the chest with the help of a computer program;

determining an averaged coefficient of specific electroconductivity for large anatomical structures of the chest on CT or MRT data based on known conformities between a type of biological tissue and a Hounsfield number at CT or between an intensity of an MR-signal at MRT and a type of the biological tissue and its specific electroconductivity;

determining coordinates of the registration electrodes on the chest surface;

interpolating values of the ECG-signals in nodes of a polygonal grid and obtaining isopotential maps on a polygonal model of the torso;

reconstructing an electric field potential at given points of the chest, the heart epicardial surface, interventricular and interatrial septum surfaces based on a model of the chest with a piecewise-constant coefficient of electroconductivity;

producing a visualization of results of reconstructing a heart electric field including epicardial electrograms, isochronous and isopotential maps and propagation maps on the polygonal models of the heart and its structures;

clinically evaluating the results.

2. The method according to claim 1, further comprising using sticky metal chlorine-silver electrodes for CT and sticky graphite electrodes for MRT.

3. The method according to claim 1, wherein the one-off electrodes are attached in the form of horizontal 5-8 belts (strips) positioned at similar distances along a vertical, a first strip being positioned at the level of a sterno-clavicular articulation and a last one being positioned at the level of lower edge of the rib surface, each strip including from 16 to 30 electrodes located at similar distances in a circumference of the chest.

4. The method according to claim 1, further comprising using a shear-warp factorization of the viewing transformation algorithm for constructing the voxel model.

5. The method according to claim 1, wherein said step of constructing the polygonal models comprises the following sub-steps:

filtrating the initial voxel models for diminishing a level of casual noises;

constructing a triangulation surface by a marching cubes method or by an advancing front method or exhaustion method;

rarefying and improving a quality of a grid using a Poisson surface reconstruction method.

6. The method according to claim 1, wherein the determining of a coefficient of specific electroconductivity at each point of the chest is carried out based on known conformities between (1) a type of the biological tissue and the Hounsfield number at CT or between an intensity of the MR-signal at MRT, and/or (2) a type of the biological tissue and a specific electroconductivity thereof.

7. The method according to claim 1, further comprising carrying out said step of determining coordinates of registration electrodes in automatic mode on the CT or MRT data of the chest.

8. The method according to claim 1, further comprising performing said step of interpolating the ECG-signal values of a polygonal grid using radial basis functions.

9. The method according to claim 1, wherein reconstructing the heart electric field potential is carried out by means of numerical solution of a Cauchy problem for a Laplace equation using a boundary element method that includes an iteration solution of a final system of matrix-vector equations, for solving those equations of the system, whose matrices are characterized by a high conditionality number, regularizing methods being applied and the total number of algorithm iterations being determined according to a principle of a residual or a Morozov principle.

10. The method according to claim 9, further comprising the step of applying a Tikhonov regularization method for solving those equations from the system of matrix-vector equations, whose matrices are characterized by a high conditionality number, and determining a regularization parameter according to the formula:

$$\alpha = \alpha_0 + \beta \cdot p^{-(k/2)}, \quad (17)$$

where $\alpha$ is a regularization parameter, $\alpha_0$ is a small real parameter depending on an error of defining boundary conditions of an inverse problem of electrocardiography, p is a positive real parameter depending on a convergence velocity of an iteration procedure, $\beta$ is a positive real parameter depending on an accuracy of an initial approximation in an iteration procedure, and k is the iteration number.

11. The method according to claim 9, wherein for solving those equations from the system of matrix-vector equations, whose matrices are characterized by a high conditionality number, a regularizing algorithm is used based on an SVD-decomposition of a matrix of the equation with substituting singular numbers that are less than a given positive number $\epsilon$ by zeroes, a parameter $\epsilon$ being determined according to the formula: $\epsilon = \epsilon_0 = \beta \cdot p^{-(k/2)}$ where $\epsilon_0$ is a small real parameter depending on an error of defining boundary conditions of an inverse problem of electrocardiography, p is a positive real parameter depending on a convergence velocity of an iteration procedure, $\beta$ is a positive real parameter depending on an accuracy of an initial approximation in an iteration procedure, and k is the iteration number.

12. The method according to claim 9, wherein for solving those equations from the system of matrix-vector equations, whose matrices are characterized by a high conditionality number, a regularizing algorithm is used based on an iterative generalized minimal residual method with restricting a number of iterations, a required number of iterations being determined according to the formula: $n = n_0 + \lambda \cdot k$ where n is a number of algorithm iterations, k is the iteration number in a total iteration procedure, $n_0$ and $\lambda$ are positive whole numbers depending on an accuracy of an initial approximation and on the convergence velocity of a procedure (11)-(13).

13. The method according to claim 9, wherein equations of the system of matrix-vector equations are solved based on the fast multipole method.

* * * * *